(12) United States Patent
Ley et al.

(10) Patent No.: US 8,592,621 B2
(45) Date of Patent: Nov. 26, 2013

(54) PRECURSOR COMPOUNDS OF SWEET TASTE RECEPTOR ANTAGONISTS FOR THE PREVENTION OR TREATMENT OF DISEASE

(75) Inventors: Jakob Peter Ley, Holzminden (DE); Michael Backes, Holzminden (DE); Tobias Vössing, Beverungen (DE); Frauke Stähler, Berlin (DE); Wolfgang Meyerhof, Norderstedt (DE); Christian Wintermeyer, Höxter (DE)

(73) Assignee: Symrise AG, Holzminden (DE)

( * ) Notice: Subject to any disclaimer, the term of this patent is extended or adjusted under 35 U.S.C. 154(b) by 412 days.

(21) Appl. No.: 12/837,012

(22) Filed: Jul. 15, 2010

(65) Prior Publication Data

US 2011/0045069 A1 Feb. 24, 2011

(30) Foreign Application Priority Data

Jul. 15, 2009 (DE) .......................... 10 2009 027 744

(51) Int. Cl.
*C07C 69/76* (2006.01)
*A01N 37/10* (2006.01)

(52) U.S. Cl.
USPC ............................................ 560/61; 514/543

(58) Field of Classification Search
None
See application file for complete search history.

(56) References Cited

U.S. PATENT DOCUMENTS 3,494,957 A 2/1970 Nakanishi et al.
4,687,849 A * 8/1987 Frater et al. ................... 544/354

FOREIGN PATENT DOCUMENTS

EP 159864 A2 10/1985
WO WO-2009026389 A2 2/2009
WO WO-2010034212 A1 4/2010

OTHER PUBLICATIONS

Hayashi et al., Agricultural and Biological Chemistry (1983), 47(11), 2653-.*
Database CAPLUS Chemical Abstracts Service, Columbus, Ohio, US; Database Accession No. 2009:846107, Abstract of Goldfarb et al., U.S. Publication No. 20090163545, Jun. 25, 2009.*
"Dosage Forms: Non-Parenteral" in Encyclopedia of Pharmaceutical Technology, 2002, Marcel Dekker, Inc., pp. 749-761.*
"High-Throughput Screening" in Ulmann's Encyclopedia of Industrial Chemistry, Rodney Turner et al., Published Online: Jun. 15, 2000, Copyright © 2002 by Wiley-VCH Verlag GmbH & Co. KgaA, pp. 699-710.*
Database CAPLUS Chemical Abstracts Service, Columbus, Ohio, US; Database Accession No. 1967:2347, Abstract of NL 6600044 Jul. 6, 1966 α-Aryloxyalkanoic Esters of Polyols.*
Database WPI Week 201027 Thomson Scientific., London, GB; AN 2010-D75022, XP002603817, Li D.; Li X.; Xu Z.: "Novel Phenoxy Acetic Acid Pyrazine Ester Derivative Useful in Pharmaceutical Composition for Reducing Blood lipid, for Reducing Serum Triglyceride level and Serum Cholesterol and for Elevating High-density Lipoprotein".

(Continued)

*Primary Examiner* — Karl J Puttlitz
(74) *Attorney, Agent, or Firm* — Dilworth & Barrese, LLP

(57) ABSTRACT

A description is given of precursor compounds of sweet taste receptor antagonists for the prevention or treatment of disease, in particular for the prevention or treatment of Type 2 diabetes.
A description is also given of uses of these precursor compounds and edible compositions, preparations for nutrition or pleasure or semi-finished products and pharmaceutical preparations, containing such precursor compounds.

17 Claims, 4 Drawing Sheets

Release of lactisole in the course of artificial digestion.

(56) References Cited

OTHER PUBLICATIONS

Heathcock, Clayton H. et al., "Acyclic stereoselection. 23. Lactaldehyde enolate equivalents," Journal of the American Chemical Society, vol. 106, No. 26, 1984, pp. 8161-8174, XP002603815.
Camps P. et al., "(R)- and (S)-3-Hydroxy-4,4-dimethyl-1-phenyl-2-pyrrolidinone as chiral auxiliaries for the asymmetric synthesis of α-hydroxy acids," Tetrahedron: Asymmetry, vol. 8, No. 11, 1997, pp. 1877-1894, XP004074674, Pergamon Press Ltd, Oxford, GB ISSN: 0957-4166.
Jiang Peihua et al., "Lactisole interacts with the transmembrane domains of human T1R3 to inhibit sweet taste," The Journal of Biological Chemistry, vol. 280, No. 15, 2005, pp. 15238-15246, XP002603816, ISSN: 0021-9258.
Extended European Search Report, EP Application No. 10169426.3, received on Nov. 1, 2010.

* cited by examiner

Figure 1: Release of lactisole in the course of artificial digestion.
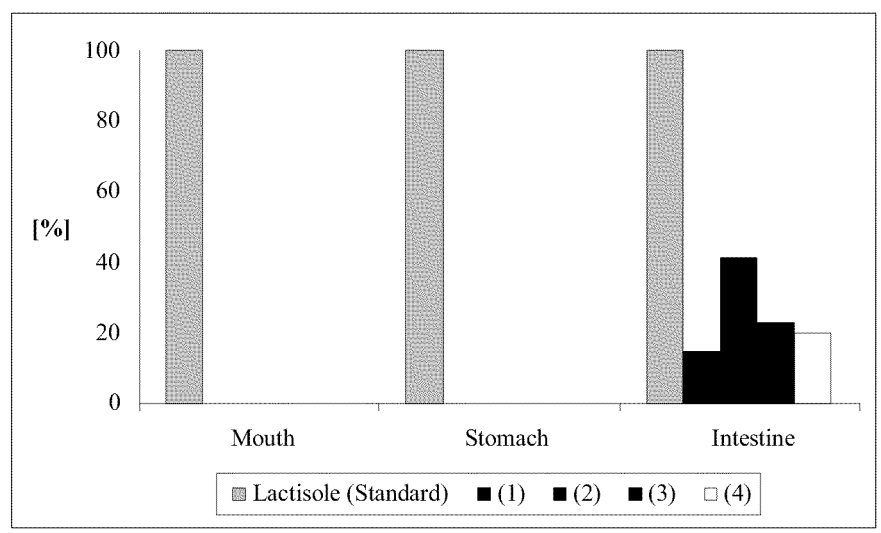

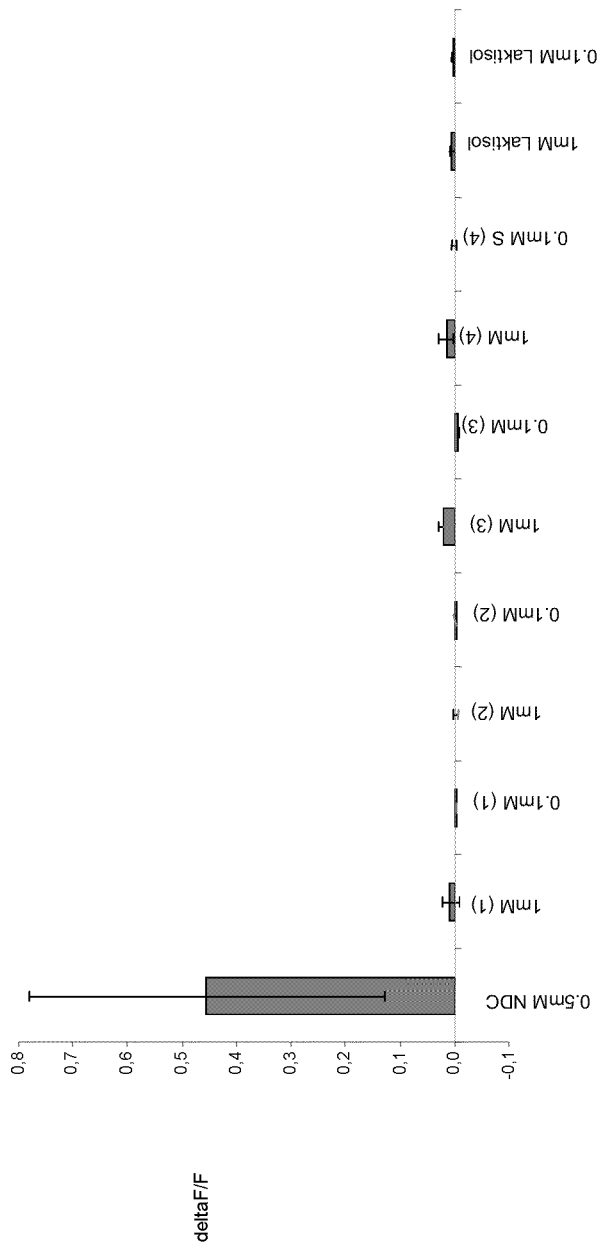
Figure 2: Comparison of the activation of TAS1R2/TAS1R3 by compounds of formulas (1) to (4), NDC, and lactisole.

Figure 3: Antagonistic effect on sweet taste receptor TAS1R2/TAS1R3 by compounds of formulas (1) and (2) in the presence of naringin dihydrochalcone (NDC).
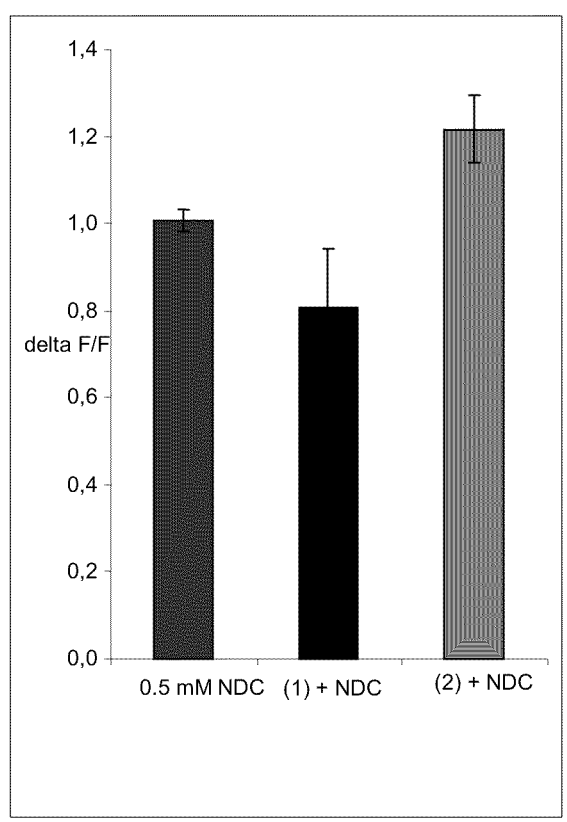

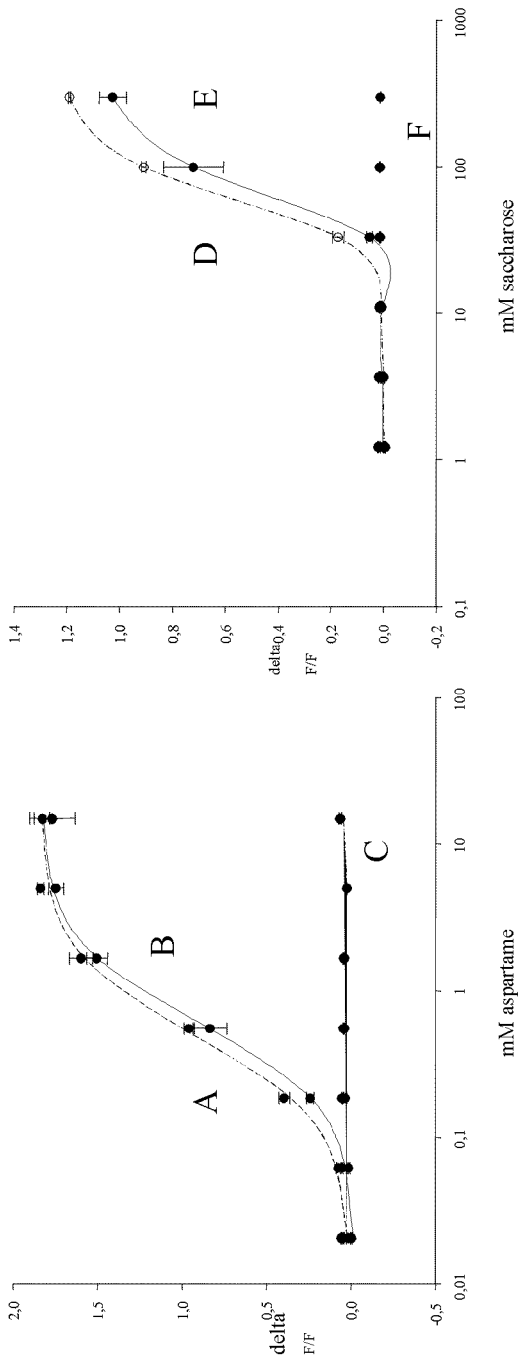
Figure 4: Antagonistic Effects on TAS1R2/TAS1R3 by lactisole derivatives 2 and 3 in the presence of aspartame or saccharose.
A = aspartame ($EC_{50}$ = 0.50 mM)
B = aspartame + 1 mM 2 ($EC_{50}$ = 0.61 mM)
C = aspartame + 1mM lactisole
D = saccharose ($EC_{50}$ = 65.7 mM)
E = saccharose + 1 mM 2 ($EC_{50}$ = 78.7 mM)
F = saccharose + 1 mM lactisole
$EC_{50}$ = average effective concentration

PRECURSOR COMPOUNDS OF SWEET TASTE RECEPTOR ANTAGONISTS FOR THE PREVENTION OR TREATMENT OF DISEASE

CROSS-REFERENCE TO RELATED APPLICATIONS

This application claims priority under 35 U.S.C. §119(a) to Patent Application No. 102009027744.7, filed in Germany on Jul. 15, 2009, the entire contents of which are hereby incorporated by reference.

The present invention concerns primary precursor compounds of sweet taste receptor antagonists, in particular of $T1R_2/T1R_3$ receptor antagonists, and mixtures thereof, for the prevention or treatment of disease, in particular for the prevention or treatment of diabetes, and quite particularly Type 2 diabetes.

The present invention also concerns precursor compounds of sweet taste receptor antagonists or mixtures thereof for reducing the absorption of glucose in the intestine, in particular in the small intestine, and/or for competitive suppression of sweet taste receptors in the intestine, in particular for competitive suppression of the T1R2/T1R3 receptors in the small intestine.

In particular the present invention concerns (for the stated purposes) those precursor compounds that are suitable for releasing lactisole in the intestine. Preferably, with these precursor compounds it is a case of compounds of formula (I),

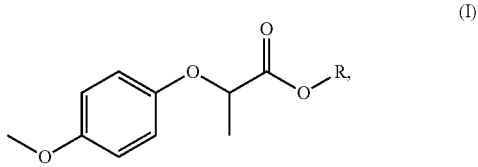

(I)

wherein the radical R denotes an aromatic or aliphatic radical. Preferred compounds of formula (I) will be described in the following.

The present invention also concerns compounds of the formula (I) and mixtures of these (as described in the following) which are new compared with the prior art.

According to a further aspect, the present invention also concerns edible compositions, preparations for nutrition or pleasure or semi-finished products and pharmaceutical preparations, comprising one or more inventive precursor compound(s).

Further aspects of the present invention, for example various uses of inventive precursor compounds, will emerge from the following description, the examples and the attached claims.

It has long been known that a raised calorie intake, in particular a raised calorie intake in the form of sweet-tasting sugars or easily decomposed carbohydrates, which quickly release glucose into the body, makes a significant contribution to the increasing incidence of diabetes, especially the incidence of Type 2 diabetes (Diabetes mellitus Type 2, formerly known as adult onset diabetes). With Type 2 diabetes there is a so-called relative insulin deficiency. While the messenger substance insulin is actually present, it is unable to operate or cannot do this adequately at its target location, the cell membranes, since the cells fail to respond or respond weakly to insulin (insulin resistance). Such insulin resistance generally precedes the manifestation of the diabetes by several years and can (apart from genetic predisposition) inter alia be intensified or caused by a constantly raised calorie intake: as a result of a constantly raised glucose level in the blood and the associated continuously high release of insulin the sensitivity to insulin of the cells is lowered due to down-regulation of the insulin receptors. In order to compensate for the reduced insulin sensitivity the pancreas produces ever-increasing quantities of insulin. After a certain time, however, the pancreas is unable to maintain this excessive insulin production because of the resultant depletion and premature necrosis of the insulin-producing islet cells in the pancreas. The amount of insulin produced is then no longer sufficient to (adequately) control the blood sugar level and Type 2 diabetes manifests itself.

Thus in the past calorie-free sugar substitutes such as sugar alcohols (e.g. fructose, erythritol [E968], isomalt [E953], isomaltulose, lactitol [E966], maltitol [E965], mannitol [E421], sorbitol [E420], trehalose, xylitol [E967]) or high intensity sweeteners (such as acesulfame K [E950], alitame, aspartame [E951], brazzein, cyclamate [E952], neohesperidine DC [E959], neotame, saccharin [E954], stevioside, and sucralose [E955] have been discussed as alternatives to glucose and used in a large number of products previously containing sugar. Due to their (in some cases very strong) sweet taste, these substances will satisfy the hedonistic need for sweetness without (disadvantageously) raising the glucose level in the blood.

Gymnemic acids from plants of the genus *Gymnema sylvestre* are already used as anti-diabetic agents (Suttisri R, Lee I-S & Kinghorn A D (1995) Plant-derived triterpenoid sweetness inhibitors. J. Ethnopharmacol., 47, 9-26).

The primary receptors and the signal cascade necessary in the taste cells or buds for signal transmission to the brain in order to allow sweet perception in the mouth, in particular on the tongue, have already been described in the prior art (Meyers B & Brewer M S (2008) Sweet taste in man: a review. Journal of Food Science, 73(6), R81-R90). According to Chandrashekar et al. (Chandrashekar J, Hoon M A, Ryba N J P & Zucker C S (2006) the receptors and cells for mammalian taste. Nature, 444(7117), 288) all the sweeteners investigated previously bind to the GPCR heterodimer (GPCR: G protein-coupled receptor) T1R2/T1R3 (Tas1R2, taste receptor, type 1, member 2/Tas1R3, tas receptor, type 1, member 3). The receptor binding or the signal transmission can be inhibited by (sweet taste receptor-)antagonists, for example lactisole, on a dose-dependent basis (Xu H, Staszewski L, Tang H, Adler E, Zoller M & Li X (2004) Different functional roles of T1R subunits in the heteromeric taste receptors. Proceedings of the National Academy of Sciences of the United States of America, 101, 14258-14263; Jiang, P., M. Cui, et al. (2005). "Lactisole Interacts with the Transmembrane Domains of Human T1R3 to Inhibit Sweet Taste." Journal of Biological Chemistry 280(18): 15238-15246). In the example of lactisole, this effect has already been documented in taste tests (Schiffmann S S, Booth B J, Sattely-Miller E A, Graham B G & Gibes K M (1999) Selective inhibition of sweetness by the sodium salt of +/−2-(4-methoxyphenoxy)propanoic acid. Chemical Senses, 24(4), 439-447). Details of the sweet taste receptor antagonist lactisole are provided further on.

According to new findings the T1R2/T1R3 receptors responsible for sweet taste reception are not only located on the tongue, but also in specialized cells in the intestinal epithelium, in particular that of the small intestine (Dyer J, Salmon K S H, Zibrik L & Shirazi-Beechey S P (2005) Expression of sweet taste receptors of the T1R family in the intestinal tract and enteroendocrine cells. Biochemical Society Transactions, 33(1), 302-305). Apart from the heterodimer T1R2/T1R3 the entire signal cascade known for the sweet taste (alpha-gustducin, phospholipase C-beta 2, TRPM5) has been found in the "Solitary Intestinal Epithelial Cells" of the small intestine in humans (Bezençon C, le Coutre J & Damak S (2007) Taste-Signaling Proteins Are Coexpressed in Solitary Intestinal Epithelial Cells. Chem. Sens., 32(1), 41-49). It is also known that (in rats at least) hormones are also secreted from these cells which inter alia may stimulate the glucose absorption from the intestine through GLUT-2 (glucose transporter isoform 2) or via the regulator SGLT1 (sodium-dependent glucose transporter isoform 1), i.e. indirectly increase the blood sugar level (Mace O J, Affleck J, Patel N & Kellett G L (2007) Sweet taste receptors in rat small intestine stimulate glucose absorption through apical GLUT2. Journal of Physiology, 582(1), 379-392 and Margolskee R F, Dyer J, Kokrashvili Z, Salmon K S H, Ilegems E, Daly K, Maillet E L, Ninomiya Y, Mosinger B & Shirazi-Beechey S P (2007) T1R3 and gustducin in gut sense sugars to regulate expression of Na+-glucose cotransporter 1. Proceedings of the National Academy of Sciences of the United States of America, 104(38), 15075-15080).

According to the prior level of knowledge sweet taste receptors in the tongue, with regard to their selectivity, do not differ from those in the (small) intestine. This does indeed mean that sweet taste receptor antagonists, for example lactisole, gurmarin or gymnemic acid (see below, WO 2009/026389 A2) as a rule (may) inhibit both the sweet taste receptors in the oral cavity and the sweet taste receptors in the intestine. However, such sweet taste receptor antagonists are less suitable for use in foodstuffs, in particular for use in primary sweet tasting foodstuffs, for the purpose of inhibiting sweet taste receptors in the intestine precisely because of their taste modifying effect, that is the reduction of the sweet taste impression in the oral cavity.

In the recently published WO 2009/026389 A2 methods are disclosed which through the use of sweet taste inhibitors (for example lactisole, gurmarin, gymnemic acid, substituted sulfamates and substituted cyclamate-sulfamates) or sweet taste potentiators allow the sweet taste receptors to be influenced (an intensification or an inhibition) in the intestine. In this connection, a way is also described (in oral application) of preventing the taste cells in the oral cavity from being influenced. For this purpose the sweet taste receptor antagonists are encapsulated in a pharmaceutical excipient, which releases the sweet taste receptor antagonists in the stomach, in the small or in the large intestine, wherein the pharmaceutical excipient can be fashioned in such a way that contact between the sweet taste receptor antagonists and the taste cells in the oral cavity is essentially prevented. In WO 2009/026389 A2, however, no precursors (precursor compounds) of sweet taste receptor antagonists, in particular no precursor compounds of lactisole, are described, which through the endogenic digestion are only metabolized in the stomach into an (active) sweet taste receptor antagonist and if necessary other compounds permitted or suitable for use in food.

The primary object of the present invention was to provide pharmaceutical formulations or substances (compounds) in the use of which, the sweet taste receptors in the intestine, in particular in the small intestine, can be selectively inhibited, without (adversely) influencing the sweet taste receptors in the oral cavity. Here in particular it was a case of finding pharmaceutical formulations or substances which are ideally (virtually) tasteless and preferably also do not influence the taste impression of other substances in the oral cavity. Preferably substances should be provided which are particularly suitable for direct processing in foods and do not require any further formulation (e.g. gastric juice-resistant encapsulation).

In particular such pharmaceutical formulations or substances should be provided which are suited to the prevention or treatment of diabetes, in particular of Type 2 diabetes.

A further object of the present invention was to provide corresponding edible compositions, preparations for nutrition or pleasure and pharmaceutical preparations, in particular pharmaceutical preparations for oral application.

Further objects of the present invention will emerge from the present description, the examples and in particular the attached claims.

The primary object of the present invention is achieved by a precursor compound of a sweet taste receptor antagonist, in particular a T1R2/T1R3 receptor antagonist, or a mixture of two or more precursor compounds of one or more different sweet taste receptor antagonists, in particular one or more different T1R2/T1R3 receptor antagonists, wherein the, or one, more or all precursor compounds is or are suitable for releasing in the intestine one or more different sweet taste receptor antagonists, in particular one or more different T1R2/T1R3 receptor antagonists, for the prevention or treatment of disease, with the proviso that the individual precursor compound is neither a compound of formula (X1) nor a compound of formula (X2) and the mixture is not a mixture of a compound of formula (X1) and a compound of formula (X2)

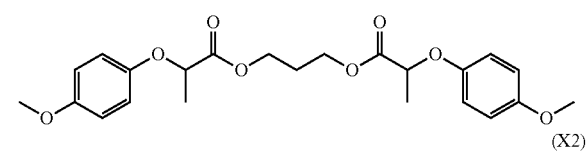

(X1)

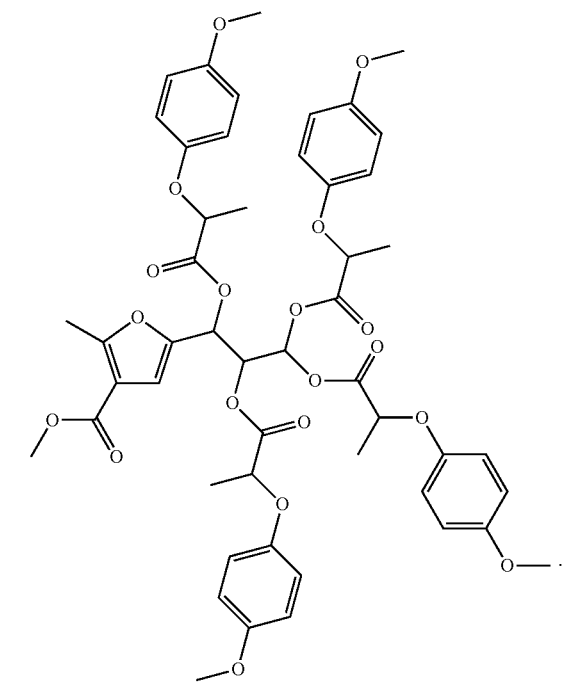

(X2)

In addition, it is preferable for an inventive mixture (as described above) not to contain both a compound of formula (X1) and a compound of formula (X2). It is also preferable for an inventive mixture (as described above) to contain neither a compound of formula (X1) nor a compound of formula (X2).

The compounds of formulas (X1) and (X2) are already described in the prior art as compounds which can be used to lower the cholesterol level (see below). Consequently, the compounds of formulas (X1) and (X2) for the prevention or treatment of disease, in particular for lowering the cholesterol level, are not a subject matter of the present invention.

Use of compounds of formulas (X1) and (X2) (see above) for the prevention or treatment of diabetes and/or to lower the absorption of glucose in the intestine and/or for competitive suppression of sweet taste receptors in the intestine, in particular for competitive suppression of the T1R2/T1R3 receptors in the small intestine, is not described in the prior art, however. The compounds of formulas (X1) and (X2) are consequently inventive (precursor) compounds for the prevention or treatment of diabetes, in particular of Type 2 diabetes, or for reducing the absorption of glucose in the intestine, in particular in the small intestine, and/or for competitive suppression of sweet taste receptors in the intestine, in particular for competitive suppression of the T1R2/T1R3 receptors in the small intestine (as described in the following).

A further (preferred) aspect of the present invention concerns in particular a precursor compound of a sweet taste receptor antagonist, in particular of a T1R2/T1R3 receptor antagonist, or a mixture of two or more precursor compounds of one or more different sweet taste receptor antagonists, in particular of one or more different T1R2/T1R3 receptor antagonists, wherein the, or one, more or all precursor compounds is or are suitable for releasing in the intestine one or more different sweet taste receptor antagonists, in particular one or more different T1R2/T1R3 receptor antagonists, for the prevention or treatment of diabetes, in particular of Type 2 diabetes.

An inventive mixture for the prevention or treatment of disease or for the prevention or treatment of diabetes, in particular of Type 2 diabetes, (as described in each case above) preferably comprises a) two or more different precursor compounds of one, that is to say the same, sweet taste receptor antagonist and/or b) two or more different precursor compounds of different sweet taste receptor antagonists. Consequently, the precursor compounds inventively contained in such a mixture are either suitable for releasing a) one, that is to say the same, sweet taste receptor antagonist or b) different sweet taste receptor antagonists in the intestine. In addition, an inventive mixture of various stereoisomers, especially various enantiomers and/or diastereomers, can contain or comprise one or more precursor compounds. Further, the precursor compounds contained in an inventive mixture can be suitable for releasing various stereoisomers, especially various enantiomers and/or diastereomers, of one or more (different) sweet taste receptor antagonists in the intestine.

Particular preference is for an inventive precursor compound or mixture of two or more precursor compounds (as described above) a precursor compound or a mixture for reducing the absorption of glucose in the intestine, in particular in the small intestine, and/or competitive suppression of sweet taste receptors in the intestine, in particular for competitive suppression of the T1R2/T1R3 receptors in the small intestine.

According to the invention, precursor compounds of lactisole are particularly preferred for the purposes of prevention or treatment of diabetes, in particular of Type 2 diabetes. Consequently, an inventive precursor compound or a mixture of two or more precursor compounds (for the treatment of diabetes, in particular of Type 2 diabetes, as described above) is particularly preferred, wherein the precursor compound or one, more or all precursor compounds of the mixture is or are a lactisole-precursor compound or lactisole-precursor compounds and is or are suitable for releasing lactisole in the intestine.

The sweet taste receptor inhibiting effect of lactisole has already been described above. Lactisole(2-(4-methoxyphenoxy)propanoic acid; CAS-Number [13794-15-5]) and various derivatives as well as salts of these have furthermore been known for a long time as taste modulators. For example, the sodium salt of lactisole was registered with the FEMA (Flavor & Extract Manufacturers Association) under number 3773 and has since then held GRAS status (Generally Recognized As Safe) for use in food. In EP 159864, for example, the use of this sodium salt for reducing the inherent sweet taste of various sugary foods is disclosed.

Furthermore, lactisole has been detected in roasted Arabica coffee beans from Columbia (in concentrations of between 0.55 ppm and 1.2 ppm) (Rathbone E B, Patel G D, Butters R W, Cookson D, Robinson J L (1989); Occurrence of 2-(4-Methoxyphenoxy)propanoic Acid in Roasted Coffee Beans: Analysis by Gas-Liquid Chromatography and by High-Performance Liquid Chromatography. J. Agric. Food Chem. 37, 54-58). According to a further publication the lactisole detected in this occurs predominantly (up to approximately 80%) in the (S)-configured form (Rathbone E B, Butters R W, Cookson D, Robinson J L (1989); Chirality of 2-(4-Methoxyphenoxy)propanoic Acid in Roasted Coffee Beans: Analysis of the Methyl Esters by Chiral High-Performance Liquid Chromatography. J. Agric. Food Chem. 37, 58-60).

In the prior art, various lactisole esters have also been described. In particular methyl-, ethyl- and n-butyl esters are known as synthesis building blocks. The various publications also deal with the isolation of optically active lactisole or corresponding esters thereof. Apart from an asymmetrical synthesis (e.g. Chen C, Zhu S F, Liu B, Wang L X & Zhou Q L (2007) Highly Enantioselective Insertion of Carbenoids into O—H Bonds of Phenols: An Efficient Approach to Chiral alpha-Aryloxycarboxylic Esters. J. Am. Chem. Soc. 129(42) 12616-12617) in the prior art manufacture through racemate splitting has also been described (e.g. Nishigaki T, Yasufuku Y, Murakami S, Ebara Y & Ueji S I (2008) A Great Improvement of the Enantioselectivity of Lipase-Catalyzed Hydrolysis and Esterification Using Co-Solvents as an Additive. Bull. Chem. Soc. Jpn 81(5) 617-622).

In WO 2004/002925 the synthesis of enantiomer pure (R)-aryloxypropionic acid esters (e.g. of (R)-lactisole ethyl ester) using (S)-alkyl O-arylsulfonyl lactates is described. Inventive precursor compounds of sweet taste receptor antagonists for the prevention or treatment of disease, in particular for the prevention or treatment of diabetes (Type 2), are not described, however.

In EP 0 528 268 the manufacture and use of various lactisole esters as solid or liquid crystalline optically anisotropic media is described. The alcoholic ester components here are predominantly biphenyls, as shown by way of example in the following graphic formula:

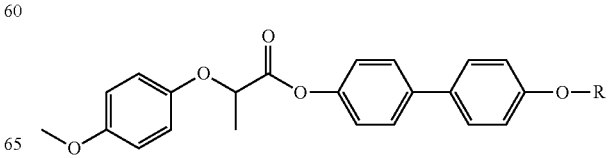

Oral administration of the lactisole esters described in EP 0 528 268 is not envisaged, however. Inventive precursor compounds of sweet taste receptor antagonists for the prevention or treatment of disease, in particular for the prevention or treatment of diabetes (Type 2), are not described in EP 0 528 268.

U.S. Pat. No. 4,687,849 describes a compound of formula:

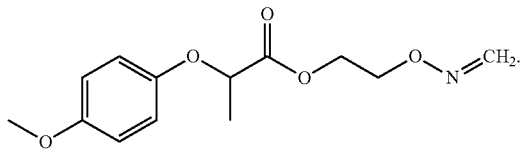 [SMILES: C=NOCCOC(=O)C(C)Oc1ccc(OC)cc1]

The enzymatic hydrolysis of certain lactisole esters for isolation of the corresponding optically active compounds is described, inter alia, in EP 0 214 569.

Inventive precursor compounds of sweet taste receptor antagonists for the prevention or treatment of disease, in particular for the prevention or treatment of diabetes (Type 2), are not described in the documents, however.

Furthermore, in the abovementioned documents nothing is said about the sensory properties of the said lactisole esters or derivates nor about their (medicinal) effect when taken orally.

In JP 43018536, JP 43012352 and JP 43002330 (see also U.S. Pat. No. 3,494,957) polyester diverse lactisole derivates (see for example the following two graphic formulas) are described, which can be used for lowering the cholesterol level.

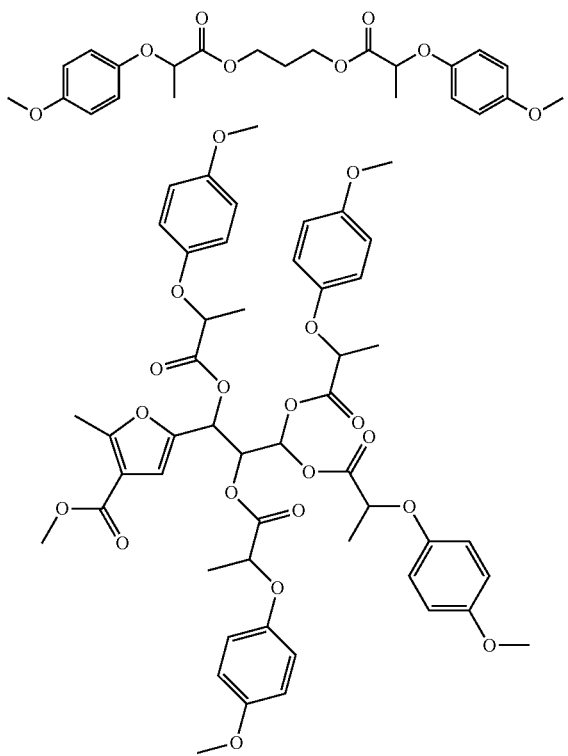

The compounds in the two graphic formulas shown above have already been referred to above in connection with an inventive precursor compound or mixture for the prevention or treatment of disease in general (denoted there as compounds of formulas (X1) and (X2)).

The compounds of general formula

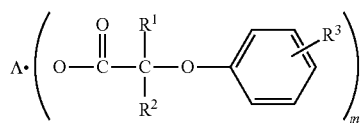

(as described in U.S. Pat. No. 3,494,957), in which $R^1$ denotes methyl, $R^2$ methyl or ethyl and $R^3$ H, Cl, methyl or methoxy, are not (inventive) precursor compounds within the meaning of the present invention.

Other lactisole esters described in the prior art are the compounds of formulas

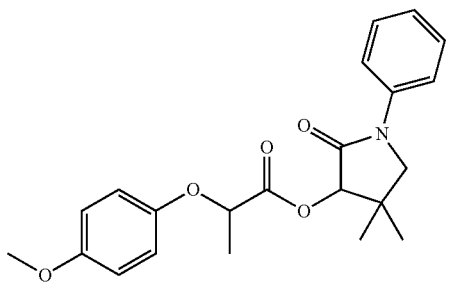

(Camps P, Perez F, Soldevilla N (1997) Asymmetric synthesis of α-hydroxy acids using (R)— and (S)-3-hydroxy-4,4-dimethyl-1-phenyl-2-pyrrolidinone as chiral auxiliaries. Tetrahedron: Asymmetry 8(11), 1877-1894)

and

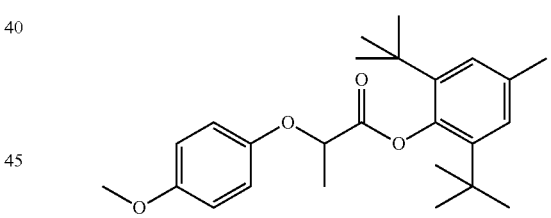

(Heathcock, C H, Pirrung M C, Young S D, Hagen J P, Jarvi E T, Badertscher U, Marki H P, Montgomery S H (1984) Acyclic stereoselection. 23. Lactaldehyde enolate equivalents. Journal of the American Chemical Society 106(26), 8161-74).

Particularly advantageous for the stated purposes and thus in the context of the present invention particularly preferred is an inventive precursor compound or a mixture of two or more precursor compounds (as described above), wherein the or one, more or all (lactisole-)precursor compound(s) is or are selected from the groups comprising compounds of formula (I)

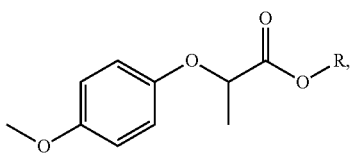

(I)

wherein the radical R of the compound of formula (I) or the radicals R of the various compounds of formula (I) independently of one another denotes or denote an aromatic or aliphatic radical. Compounds of formula (I) which are new compared with the prior art will be described further below.

The chiral centre of the lactisole group(s) of a lactisole precursor compound (as described above), in particular of a compound according to formula (I) (as described above), can in each case be (R)- or (S)-configured. An inventive mixture, especially an inventive mixture for the prevention or treatment of diabetes, in particular of Type 2 diabetes, (as described above) contains or comprises consequently preferably various enantiomers of one or more lactisole precursor compounds, wherein the various enantiomers are in each case present in the mixture in racemic, that is to say equimolar, or any other arbitrary proportions.

According to the invention, particular preference is for an inventive precursor compound or a mixture of two or more precursor compounds (as described above), wherein the radical R of the compound of formula (I) or one, more or all radicals R of the various compounds of formula (I) independently of one another, contains or contain one or more —O— groups which in each case independently of one another is or are a component of a hydroxy, ester or ether group.

Particularly preferably, the radical R of the compound of formula (I) or one, more or all radicals R of the various compounds of formula (I) contains or contain one or (preferably) more —O— groups, which is or are a component of an ester group. Quite particularly preferably via such an ester group in each case a (further) lactisole group (2-(4-methoxyphenoxy)propionyloxy-) is bonded.

As described above, the inventive precursor compounds are advantageously suited to the release in the intestine of one or more different sweet taste receptor antagonists, preferably one or more different T1R2/T1R3 receptor antagonists (for example lactisole). Apart from the sweet taste receptor antagonists—for example in the event of splitting by lipases (as described below)—in the (small) intestine one or more further components, in particular alcohols, are released (for preferred components released in the intestine, see below), wherein the further components are preferably approved for use in food and/or pharmaceutical preparations. Thus, with inventively preferred compounds of formula (I)

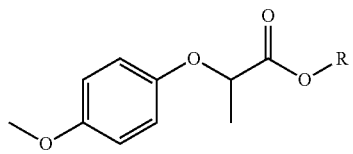

(I)

apart from lactisole routinely a compound R—OH is released, wherein the compound R—OH is an aliphatic or aromatic compound with one or more hydroxyl groups.

With compounds of formula (I) which are particularly preferred according to the invention with two or more lactisole groups (as described above), e.g. with compounds of formula (I), in which the radical R contains one or more ester groups, via which a (further) lactisole group is bonded, routinely (for each molecule of a compound of formula (I)) two or more molecules of lactisole are released.

The other components released in the (small) intestine, in particular the compounds R—OH, are preferably selected from the group comprising the following compounds (the four-digit FEMA number and the CAS number or E-number are given in brackets where these are available):

4-allyl-2,6-dimethoxyphenol [3655; 6627-88-9], 1-pentanol [2056; 71-41-0], 2-amyl-3-phenyl-2-propen-1-ol [2065; 101-85-9], 4-methoxybenzyl alcohol [2099; 105-13-5], benzyl alcohol [2137; 100-51-6], borneol [2157; 464-43-7, 507-70-0], 1-butanol [2178; 71-36-3], campholene alcohol [3741; 1901-38-8], carvacrol [2245; 499-75-2], carveol [2247; 2102-59-2, 99-48-9], carvomenthol [3562; 499-69-4], chavicol [4075; 501-92-8], cinnamyl alcohol [2294; 104-54-1], citronellol [2309; 106-22-9], 1-alpha-citronellol [2980; 6812-78-8], o-cresol [3480; 95-48-7], m-cresol [3530; 108-39-4], p-cresol [2337; 106-44-5], cymenol [3242; 1197-01-9]; decadienol [3911; 18409-21-7]; 1-decanol [2365; 112-30-1], 3-decanol [3605; 1565-81-7]; 1-decen-3-ol [3824; 51100-54-0]; (E)-2-decen-1-ol [4304; 22104-80-9]; (Z)-4-decen-1-ol [4349; 57074-37-0], dehydrodihydroionol [3446; 57069-86-0], dihydrocarveol [2379; 619-01-2], dihydroeugenol [3598; 2785-87-7], dihydrofarnesol [4031; 51411-24-6], dihydroionol [3627; 3293-47-8], syringol [3137; 91-10-1], dimethylbenzyl alcohol [3139; 536-50-5], 4-(1,1-dimethylethyl)phenol [3918; 98-54-4], 2,6-dimethyl-4-heptanol [3140; 108-82-7], 2,6-dimethyl-6-hepten-1-ol [3663; 36806-46-9], dimethylnonadienol [4102; 67845-50-5], 3,7-dimethyl-1-octanol [2391; 203-374-5], hotrienol [3830; 20053-88-7], 2-hydroxy-2-methyl-1-phenylpropane [2393; 100-86-7]; 2-hydroxypiperitone [4143; 490-03-9], 1-dodecanol [2617; 112-53-8], 2-(ethoxymethyl)phenol [3485; 20920-83-6], ethanol [2419; 64-17-5], ethyl maltol [3487; 4940-11-8], 2-(3-ethoxy-4-hydroxyphenyl)-4-methyl-1,3-dioxolane [3838; 68527-76-4], 4-ethyl syringol [3671; 14059-92-8], ethyl guaiacol [2436; 2785-89-9]; 2-ethyl-1-hexanol [3151; 104-76-7], 3-ethyl-2-hydroxy-2-cyclopenten-1-one [3152; 21835-01-8]; 4-ethyl phenol [3156; 123-07-9], 3-ethyl thio butan-1-ol [4282; 117013-33-9], 2-ethyl fenchol [3491; 18368-91-7], eugenol [2467; 97-53-0], farnesol [2478; 4602-84-0], fenchol [2480; 1632-73-1], furfuryl alcohol [2491; 98-00-0], geraniol [2507; 106-24-1], glycerin [2525; 56-81-5], glyceryl monooleate [2526; 25496-72-4], guaiacol [2532; 90-05-1], (E,E)-hepta-2,4-dien-1-ol [4127; 33467-79-7], 2-heptanol [3288; 543-49-7], 3-heptanol [3547; 589-82-2], (Z)-4-hepten-1-ol [3841; 6191-71-5], 1-hepten-3-ol [4129; 4938-52-7], 1-heptanol [2548; 111-70-6], 1-hexadecanol [2554; 36653-82-4], (E,E)-hexa-2,4-dien-1-ol [3922; 111-28-4], 1-hexanol [2567; 111-27-3], 3-hexanol [3351; 623-37-0], 1-hexen-3-ol [3608; 4798-44-1], (E)-2-hexen-1-ol [2562; 2305-21-7], (Z)-2-hexenol [3924; 928-94-9], (Z)-3-hexen-1-ol [2563; 928-96-1], (E)-3-hexen-1-ol [4356; 928-97-2]; 5-hexen-1-ol [4351; 821-41-0], (E)-4-hexen-1-ol [3430; 928-92-7], (Z)-4-hexen-1-ol [3430; 928-91-6]; 4-hydroxybenzyl alcohol [3987; 623-05-2], hydroxycitronellol [2586; 107-74-4], alpha-ionol [3624; 25312-34-9], beta-ionol [3625; 22029-76-1]; isoamyl alcohol [2057; 123-51-3]; isoborneol [2158; 124-76-5]; isobutyl alcohol [2179; 78-83-1]; 4-methyl-1-phenyl-2-pentanol [2208; 7779-78-4]; isochavicol [4062; 539-12-8], isoeugenol [2468; 97-54-1], 2-propanol [2929; 67-63-0]; cuminol [2933; 536-60-7], o-cumenol [3461; 88-69-7], isopulegol [2962; 89-79-2], linalool oxide [3746; 1365-19-1, 5989-33-3], linalool [2635; 78-70-6], maltol

[2656; 118-71-8], menthol [2665; 15356-60-2, 1490-04-6, 2216-51-5], 2-(l-menthoxy)ethanol [4154; 38618-23-4], menthyl lactate [3748; 59259-38-0], p-menthane-3,8-diol [4053; 42822-86-6], (−)-3-menthoxypropane-1,2-diol [3784; 87061-04-9], mercaptobutanol [3502; 37887-04-0], 3-mercaptohexanol [3850; 51755-83-0], 3-mercapto-2-methyl-1-butanol [3993; 227456-33-9]; 3-mercapto-3-methyl-1-butanol [3854; 34300-94-2]; 2-mercapto-2-methyl-1-pentanol [3995; 258823-39-1], 3-mercapto-2-methyl-1-pentanol [3996; 227456-27-1], 4-mercapto-4-methyl-2-pentanol [4158; 31539-84-1], creosol [2671; 93-51-6]; 4-vinyl guaiacol [2675; 7786-61-0], 2-methylbutan-1-ol [3998; 137-32-6], 3-methyl-2-butanol [3703; 598-75-4], 2-methylbut-2-en-1-ol [4178; 4675-87-0], prenol [3647; 556-82-1], 4-methyl-2,6-dimethoxyphenol [3704; 6638-05-7], 3-methyl-1-pentanol [3762; 589-35-5]; 2-phenyl-1-propanol [2732; 1123-85-9], 2-methyl-4-phenyl-2-butanol [3629; 103-05-9], 4-(methylthio)-butanol [3600; 20582-85-8], 2-(methylthio)ethanol [4004; 5271-38-5]; 3-methylthio-1-hexanol [3438; 51755-66-9], thioguaiacol [3210; 1073-29-6], 3-(methylthio)-propanol [3415; 505-10-2], myrtenol [3439; 515-00-4], neomenthol [2666; 2216-52-6], nerol [2770; 106-25-2], nerolidol [2772; 142-50-7, 7212-44-4, 40716-66-3], (3E,6Z)-nonadien-1-ol [3884; 53046-97-2]; (3Z,6Z)-nonadien-1-ol [3885; 76649-25-7], 2,6-nonadien-1-ol [2780; 7786-44-9], 2,4-nonadien-1-ol [3951; 62488-56-6], (2E,6Z)-nonadien-1-ol [2780; 28069-72-9], nonan-2-ol [3315; 628-99-9], nonan-1-ol [2789; 143-08-8], (Z)-2-nonen-1-ol [3720; 41453-56-9], (Z)-6-nonen-1-ol [3465; 35854-86-5], (E)-2-nonen-1-ol [3379; 31502-14-4], nopol [3938; 128-50-7], (E,E)-2,4-octadien-1-ol [3956; 18409-20-6], octan-1-ol [2800; 111-87-5], octan-2-ol [2801; 123-96-6], octan-3-ol [3581; 589-98-0], (E)-2-octen-1-ol [3887; 18409-17-1], (E)-2-octen-4-ol [3888; 4798-61-2], 1-octen-3-ol [2805; 3391-86-4], 3-octen-2-ol [3602; 76649-14-4], (Z)-3-octen-1-ol [3467; 20125-84-2], (Z)-5-octen-1-ol [3722; 64275-73-6], (Z)-4-octen-1-ol [4354; 54393-36-1], oleyl alcohol [4363; 143-28-2], 2-pentanol [3316; 6032-29-7], 1-penten-3-ol [3584; 616-25-1], cis-2-pentenol [4305; 1576-95-0], perilla alcohol [2664; 536-59-4], 2-phenethyl alcohol [2858; 60-12-8], phenol [3223; 108-95-2], 4-phenyl-2-butanol [2879; 2344-70-9], 4-phenyl-3-buten-2-ol [2880; 17488-65-2], 1-phenyl-3-methyl-3-pentanol [2883; 10415-87-9], 5-phenylpentanol [3618; 10521-91-2], 2-phenylphenol [3959; 90-43-7], 1-phenyl-1-propanol [2884; 93-54-9], 3-phenyl-1-propanol [2885; 122-97-4], phytol [4196; 150-86-7], pinocarveol [3587; 5947-36-4], p-menth-1-en-3-ol [3179; 491-04-3], 1-propanol [2928; 71-23-8], 4-propenyl-2,6-dimethoxyphenol [3728; 20675-95-0], 2-ethoxy-5-(1-propenyl)phenol [2922; 94-86-0], propylene glycol mono- and diesters of fatty acids [4208], propylene glycol stearate [2942; 142-75-6], propylene glycol [2940; 57-55-6], 1-phenyl-2-pentanol [2953; 705-73-7], 2-propyl phenol [3522; 644-35-9], 4-propyl phenol [3649; 645-56-7], 4-propyl-2,6-dimethoxyphenol [3729; 6766-82-1], 3-hydroxyphenol [3589; 108-46-3], rhodinol [2980; 6812-78-8], 4-thujanol [3239; 546-79-2], santalol [3006; 11031-45-1, 115-71-9, 77-42-9], sorbitol [3029; 50-70-4; E420], sotolon [3634; 28664-35-9], styrallyl alcohol [2685; 98-85-1], 4-methyl-5-thiazoleethanol [3204; 137-00-8], p-menth-3-en-1-ol [3563; 586-82-3], 1-p-menthen-4-ol [2248; 562-74-3], p-menth-8-en-1-ol [3564; 138-87-4], p-menth-1-en-8-ol [3045, 98-55-5], tetrahydrofurfuryl alcohol [3056; 97-99-4], 3,7-dimethyloctan-3-ol [3060; 78-69-3], 1-isopropyl-4-methylbicyclo[3.1.0]hexan-3-ol [4079; 21653-20-3], thymol [3066; 89-83-8], 3,3,5-trimethylcyclohexan-3-ol [3962; 116-02-9], 3,5,5-trimethyl-1-hexanol [3324; 3452-97-9], 2,4,8-trimethylnona-3,7-dien-2-ol [4211; 479547-57-4], 2,4,8-trimethyl-7-nonen-2-ol [4212; 437770-28-0], 2,3,4-trimethyl-3-pentanol [3903; 3054-92-0], 2,3,6-trimethylphenol [3963; 2416-94-6], 2,4,6-trimethylphenol [4329; 527-60-6], 2-undecanol [3246; 1653-30-1], trans-undec-2-en-1-ol [4068; 37617-03-1], 1-undecanol [3097; 112-42-5], vanillin butylene glycol acetal [4023; 4359-31-3], vanillin menthoxypropane diol acetal [3904; 180964-47-0], vanillin propylene glycol acetal [3905; 68527-74-2], vanillyl alcohol [3737; 498-00-0], 2-pinen-4-ol [3594; 473-67-6], vetiverol [4217; 89-88-3], 4-vinylphenol [3739; 2628-17-3], 2,5-xylenol [3595; 95-87-4], 2,6-xylenol [3249; 576-26-1], 3,4-xylenol [3596; 95-65-8], 2',4',6'-trihydroxy-3-(p-hydroxyphenyl)propiophenone [4390; 60-82-2], (+/−)-ethyl-3-hydroxy-2-methyl butyrate [4391; 27372-03-8], 2,4-dimethyl-4-nonanol [4407; 74356-31-3], 8,9-p-menthen-1,2-diol [4409; 1946-00-5], decahydro-2,2,4,8-tetramethyl-4,8-methanoazulen-9-ol [4410; 56747-96-7], d-2,8-p-menthadien-1-ol [4411; 22771-44-4], (Z)-3-nonen-1-ol [4412; 10340-23-5], 3,4-dihydroxybenzoic acid [4430; 99-50-3], 3-hydroxybenzoic acid [4431; 99-06-9], 2-hydroxy-4-methoxybenzaldehyde [4435; 673-22-3], methyl 3-hydroxybutyrate [4450; 1487-49-6], ethyl 3-hydroxyoctanoate [4453; 7367-90-0], hydroxyacetone [4462; 116-09-6], 1-hydroxy-4-methyl-2-pentanone [4463; 68113-55-3], propylene glycol mono-2-methylbutyrate [4467; 923593-56-0 & 923593-57-1], propylene glycol monohexanoate [4469; 39556-41-7 & 170678-49-6], dodecyl lactate [4482; 6283-92-7], hexadecyl lactate [4483; 35274-05-6], hydroxycitronellal propylene glycol acetal [4485; 93804-64-9], citral glyceryl acetal [4486; 5694-82-6], propylene glycol monobutyrate [4488; 29592-95-8], 2-methoxy-6-(2-propenyl)phenol [4490; 579-60-2], (R)-(−)-1-octen-3-ol [4492; 3687-48-7], cubebol [4497; 23445-02-5], (−)-sclareol [4502; 515-03-7], (+)-cedrol [4503; 77-53-2], (D)-limonen-10-ol [4504; 38142-45-9], p-menthan-7-ol [4507; 5502-75-0], p-menth-1-en-9-ol [4508; 18479-68-0], 2,2,6,7-tetramethylbicyclo[4.3.0]nona-4,9(1)-dien-8-ol [4521; 97866-86-9], 6-hydroxycarvone [4523; 51200-86-3], 2,6,6-trimethyl-2-hydroxycyclohexanone [4531; 7500-42-7], acetoin propylene glycol acetal [4532; 94089-23-3], (+/−)-n-lactoyl tyramine [4550; 781674-18-8], magnolol [4559; 528-43-8], ethyl 2-hydroxyethyl sulfide [4562; 110-77-0], 2-hydroxyethanethiol [4582; 60-24-2], linalool oxide pyranoid [4593; 14049-11-7], 2-hydroxy-5-methylacetophenone [4594; 1450-72-2], ethyl 2-hydroxy-3-phenylpropionate [4598], (D)-trehalose [4600; 6138-23-4], (E)-3-nonen-1-ol [4605; 10339-61-4], ethyl 5-hydroxyoctanoate [4610; 75587-05-2], (Z)-2-octen-1-ol [4615; 26001-58-1], (E)-2-tridecen-1-ol [4617; 68480-25-1], 2-(phenoxy)ethanol [4620; 122-99-6], (4-methylphenyl)methanol [4624; 589-18-4], thiophen-2-ylmethanol [4642; 636-72-6], 2-hydroxy-2-(4-hydroxy-3-methoxyphenyl)acetic acid [4660; 55-10-7], (4S)-4-hydroxy-4-[(E,3R)-3-hydroxybut-1-enyl]-3,5,5-trimethylcyclohex-2-en-1-one [4661; 23526-45-6], 1-(4-hydroxy-3-methoxyphenyl)decan-3-one [4665; 27113-22-0], (2R)-6-methyl-2-[(1R)-4-methyl-1-cyclohex-3-enyl]hept-5-en-2-ol [4666; 515-69-5], mannitol [E421]; isomalt [E953]; maltitol [E965]; lactitol [E966]; xylitol [E967]; erythritol [E968]; fructose [57-48-7]; glycose [50-99-7]; sucrose [57-50-1]; ethanediol [107-21-1].

Compounds particularly preferred according to the invention are also those which can be manufactured by esterification of partially or fully hydrolyzed edible fats or oils with lactisole. Further preference is for compounds of formula (I) selected from the group comprising compounds of formula

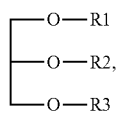

wherein one, more or all radicals R1 to R3 denote a lactisole group and the, if necessary, further radicals R1, R2 and/or R3 in each case independently of one another denote either hydrogen or another organic radical, preferably a fatty acid radical. Here, particularly preferred fatty acid radicals are selected from the group of radicals of the following fatty acids: caprylic acid, palmitic acid, stearic acid, myristic acid, oleic acid, linoleic acid, alpha-linolenic acid, gamma-linolenic acid, palmitoleic acid, margaric acid, archinic acid, lignoceric acid, elaidic acid, icosenoic acid, cetoleic acid, behenic acid, stearidonic acid, eicosapentaenoic acid, docosahexaenoic acid and arachidonic acid.

Further compounds of formula (I) that are particularly preferred according to the invention are described in Examples 1 to 6 below.

The inventive precursor compounds described in connection with the present invention, in particular the compounds of formula (I), have numerous advantages. Thus, in the course of our own investigations it was discovered that in particular the inventive (precursor) compounds of formula (I) advantageously are largely tasteless and/or do not significantly influence the taste qualities of other substances, in particular a sweet taste quality of other substances (compare here with application example 1 below).

In addition, the inventive precursor compounds, in particular the compounds of formula (I), are suitable (following oral administration) for passing through the oral cavity and the stomach without decomposing or splitting in the process. In the intestine the inventive precursor compounds then release one or more different sweet taste receptor antagonists, preferably one or more different T1R2/T1R3 receptor antagonists (compare here with application example 2 below).

The compounds of formula (I) (as described above) that are particularly preferred according to the invention are advantageously suited to releasing (almost exclusively) in the intestine, in particular in the small intestine, lactisole. According to prior knowledge this release is above all made possible by the lipases that are active in the environment of the small intestine, which in particular split the compounds of formula (I) (as described above) into lactisole and other components (in particular alcohols). This localized metabolization in the intestine advantageously enables the lactisole to selectively inhibit the sweet taste receptors in the epithelial cells of the stomach, without (for oral administration) significantly influencing the sweet taste receptors in the oral cavity.

Consequently, inventive precursor compounds (as described above) are particularly preferred which are suitable, following oral administration, for selectively releasing in the (small) intestine one or more different sweet taste receptor antagonists, in particular one or more different T1R2/T1R3 receptor antagonists, that is to say (in tests in humans) preferably without in the preceding areas of the digestive tract (Systema digestivum), i.e. in the oral cavity, in the pharynx, in the esophagus or in the stomach, releasing one of more of these different sweet taste receptor antagonists (compare here with application example 2 below).

A particular advantage of the inventive precursor compounds, in particular the compounds of formula (I), is therefore that these can be directly ingested orally, in particular through food, without significantly influencing the taste impression in the mouth, in particular without (significantly) reducing a sweet taste impression in the oral cavity, and nevertheless are suitable for releasing in a targeted manner the corresponding sweet taste receptor antagonist(s) in the intestine, so that these can deliver in a targeted manner their medicinally advantageous effect for the prevention or treatment of disease, in particular for the prevention or treatment of diabetes (Type 2), (e.g. lactisole as a sweet taste receptor antagonist for T1R2/T1R3 receptors).

The inventive precursor compounds also have the advantage over the previous substances or methods for influencing the sweet taste receptors in the intestine (e.g. as described above in connection with WO 2009/026389 A2) that they are suitable for direct processing in foods and thus allow better food technology processing than formulations which apart from a (possibly undesired) corresponding free active substance compound contain inactive ingredients and/or additives in order to prevent a premature effect. In particular, a coating of the precursor compounds in order to avoid sweet taste receptor inhibition in the oral cavity (by free sweet taste receptor antagonists) and/or to offer protection from premature metabolization (of the sweet taste receptor antagonists) is generally unnecessary. For the purposes of the present invention the endogenous digestion in the area of the (small) intestine is in fact used for the targeted release of the receptor antagonists from the precursor compounds.

In our own investigations by way of example the inventive precursor compounds manufactured by esterification of lactisole with the alcohols n-hexanol, glycerin, ethanediol and n-butanol underwent synthetic digestion (see application example 2 below). Here, it could be seen that lactisole was advantageously (almost) exclusively released in the intestine.

In addition, the inventive precursor compounds themselves, in particular the compounds of formula (I), especially the compounds of formulas (1) to (4) (see the following graphic formulas and application example 3 below), advantageously demonstrate neither a significant activation nor a significant inhibition of the T1R2/T1R3 receptors.

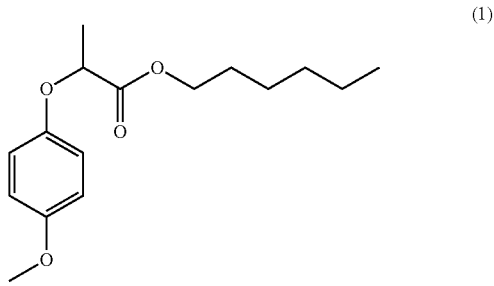

(1)

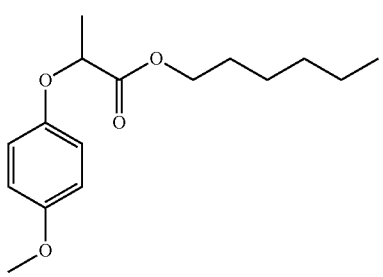
(1)

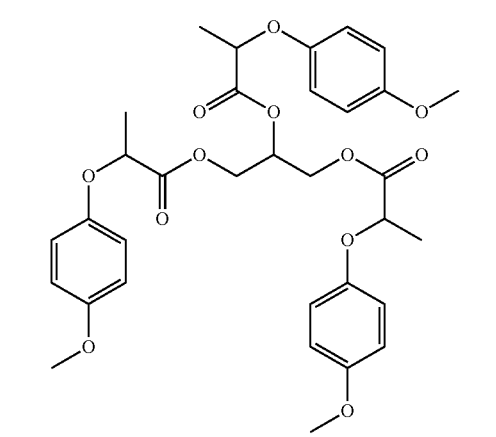
(2)

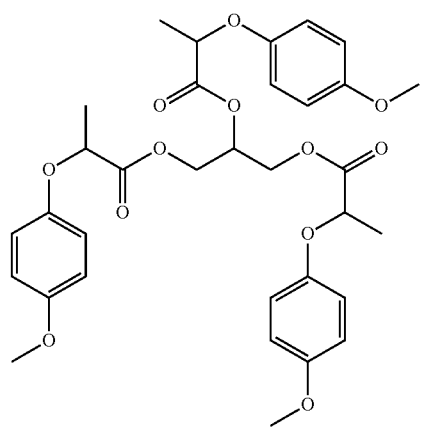
(2)

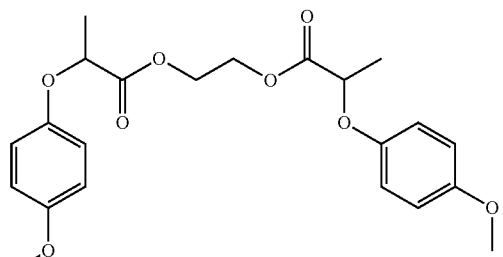
(3)

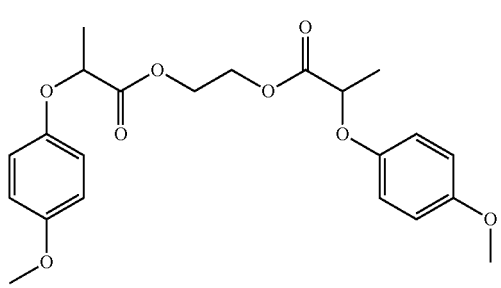
(3)

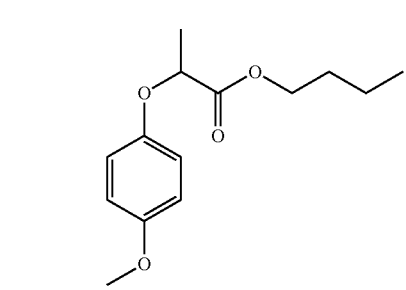
(4)

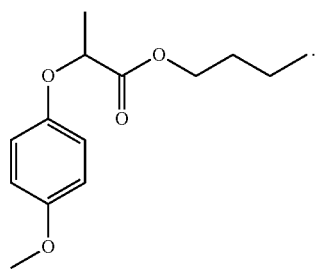
(4)

The compounds of formulas (1) to (4) are in connection with the present invention particularly preferred inventive (lactisole) precursor compounds.

Consequently, the present invention also concerns a precursor compound or a mixture of two or more precursor compounds (as described above), wherein the precursor compound or one, more or all precursor compounds in the mixture is or are selected from the group comprising 2-(4-methoxyphenoxy)propanoic acid hexyl ester (compound of formula (1)), 2-(4-methoxyphenoxy)propanoic acid-2,3-bis[2-(4-methoxyphenoxy)-propionyloxy]-propyl ester (compound of formula (2)), 2-(4-methoxyphenoxy)propanoic acid-2-[2-(4-methoxyphenoxy)-propionyloxy]-ethyl ester (compound of formula (3)), 2-(4-methoxyphenoxy)propanoic butyl ester (compound of formula (4)), 2-(4-methoxyphenoxy)propanoic acid-(E)-hex-2-enyl ester and 2-(4-methoxyphenoxy)-propanoic acid-2-isopropyl-5-methyl-phenyl ester, preferably from the group comprising the compounds of formulas (1) to (4).

Particularly advantageous for the purposes of the present invention is the compound of formula (2), so that a precursor compound or a mixture of two or more precursor compounds (as described above), wherein the precursor compound or a precursor compound of the mixture is a compound of formula (2), is particularly preferred.

A further aspect of the present invention concerns compounds of formula (I) or mixtures of two or more compounds of formula (I) which are new compared with the prior art

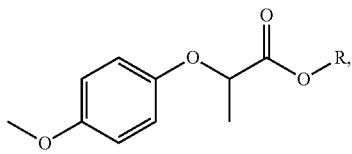
(I)

wherein the radical R of the compound of formula (I) or the radicals R of the various compounds of formula (I) independently of one another denotes or denote an aromatic or aliphatic radical.

Where in the prior art (as described above) compounds or groups of compounds are disclosed not expressly but merely in the form of a generic formula, wherein the generic formula also includes (inventive) compounds of formula (I) (as demonstrated above), the compounds of formula (I) must be considered as an inventive selection of the generic formula.

The (individual) compound or compounds or lactisole ester derivatives expressly disclosed in the prior art (as described above), which fall fully under formula (I) (as demonstrated above), are as such not a subject matter of the present invention.

According to this aspect of the present invention consequently a compound of formula (I) or a mixture of two or more compounds of formula (I) is indicated

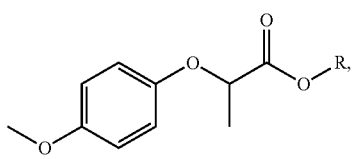
(I)

wherein the radical R of the compound of formula (I) or the radicals R of the various compounds of formula (I) independently of one another denotes or denote an aromatic or aliphatic radical, with the proviso that the individual compound of formula (I) is not selected from the group comprising compounds of formula (I), wherein the radical R denotes methyl, ethyl or butyl, compounds of formulas (X1) or (X2)

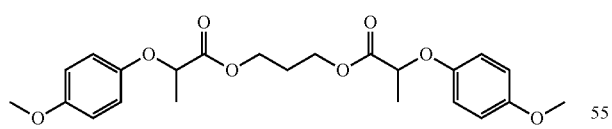
(X1)

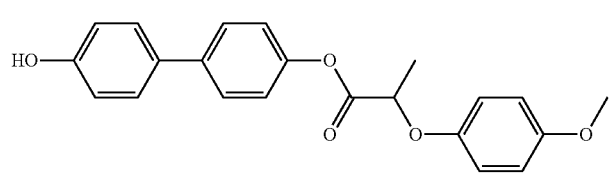

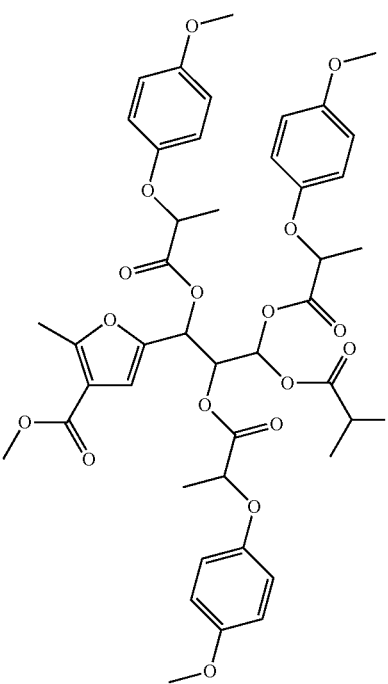
(X2)

(as described in JP 43018536, JP 43012352 and JP 43002330), compounds of formulas (X3), (X4), (X5) or (X5a)

(X3)

-continued
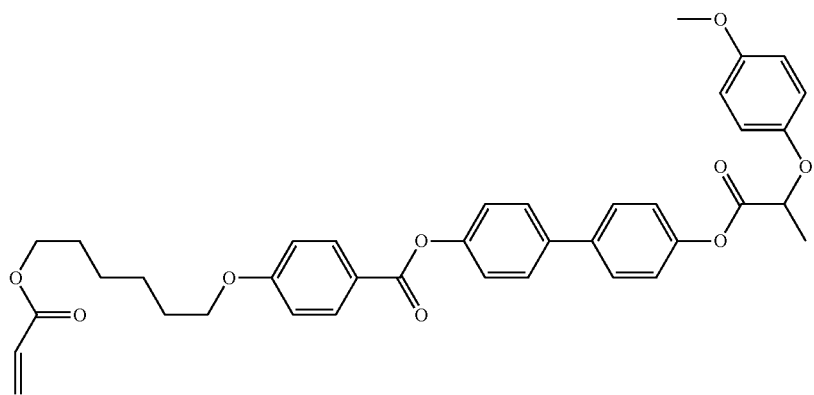
(X4)
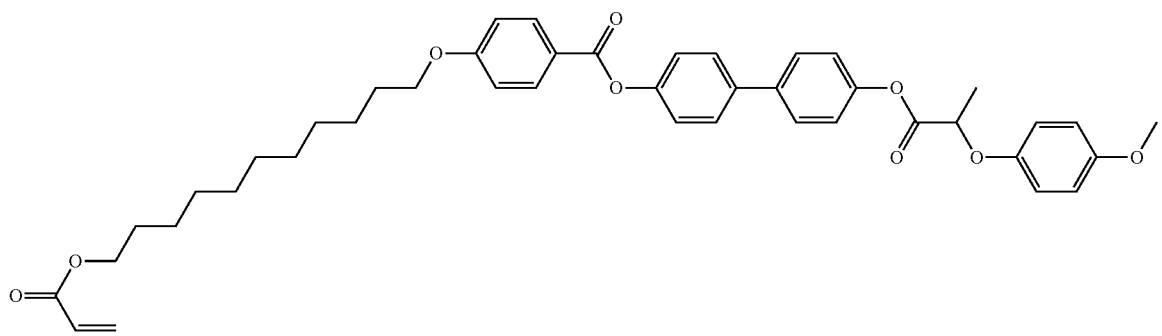
(X5)
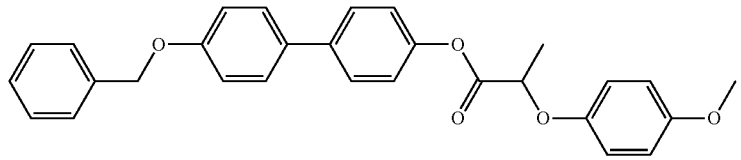
(X5a)
(as described in EP 0 528 268),
compound of formula (X6)
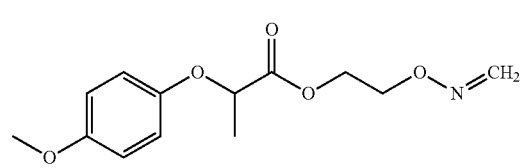
(X6)
(as described in U.S. Pat. No. 4,687,849),
compound of formula (X7)
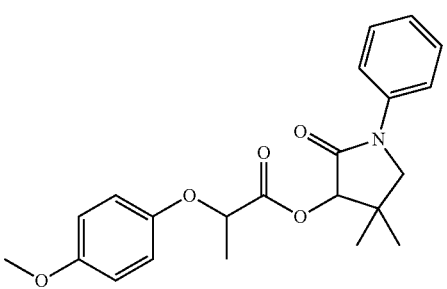 [SMILES: COc1ccc(OC(C)C(=O)OC2C(=O)N(c3ccccc3)CC2(C)C)cc1]
(X7)
(as described by Camps P Perez F. and Soldevilla N. 1997 (see above))
and
compound of formula (X8)

(X8)

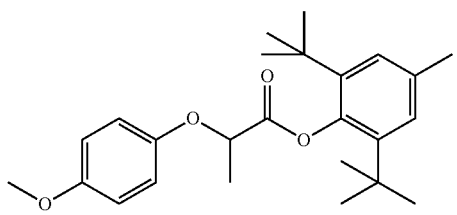

(as described by Heathcock C H, Pirrung M C, Young S D, Hagen J P, Jarvi E T, Badertscher U, Marki H P and Montgomery S H 1984 (see above)),
and,
that in the mixture not all compounds of formula (I), preferably not a plurality of compounds of formula (I), particularly preferably no compound of formula (I), is or are selected from this group, that is to say from the group comprising compounds of formula (I), wherein the radical R denotes methyl, ethyl or butyl, and compounds of formulas (X1), (X2), (X3), (X4), (X5), (X5a), (X6), (X7) or (X8).

Considering the prior art described above the following compounds are additionally not preferred:
compounds of formula (I), wherein the radical R denotes propyl, isopropyl, 1-methylpropyl or 2-methylpropyl, and
compounds of formula (I), wherein the radical R contains a biphenyl group.

Not preferred according to the invention, in consideration of the prior art described above, are also (unless otherwise indicated in the following for individual compounds) compounds of the general formula

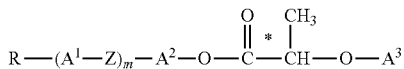

(as described in EP 0 528 268),
in which according to the description of EP 0 528 268 the indices and the variables denote as follows:
R is a $C_1$-$C_{12}$-alkyl or -perfluoroalkyl group in which, in addition, one or two non-adjacent $CH_2$ or $CF_2$ groups may be replaced by O atoms and/or —CO— groups and/or —CO—O— groups and/or —CH═CH— groups and/or —CH-halogen- and/or —CHCN— groups and/or —O—COCH-halogen- and/or —O—CO—CHCN— groups, or is a $C_1$-$C_{12}$-alkyl group which may carry a terminal chemically reactive group and in which one $CH_2$ group may be replaced by an O atom,
$A^1$ and $A^2$ independently of one another, are 1,4-phenylene which is un-substituted or substituted by one or two F and/or Cl— and/or Br atoms and/or $CH_3$ groups and/or CN groups, and in which one or two CH groups may be replaced by N, 1,4-cyclohexylene in which, in addition, one or two non-adjacent $CH_2$ groups may be replaced by O atoms and/or S atoms, piperidine-1,4-diyl, 1,4-bicyclo[2.2.2]octylene, naphthalene-2,6-diyl, decahydronaphthalene-2,6-diyl or 1,2,3,4-tetrahydronaphthalene-2,6-diyl,
$A^3$ is optionally substituted phenyl,
Z is —CO—O—, —O—CO—, —CH2CH2—, —OCH2—, —CH2O— —C≡C— or a single bond and m is 0, 1, 2 or 3, with the proviso that, if m=2 or 3, the radicals $A^1$ and Z in the individual groups -($A^1$-Z) may be identical to or different from one another.

Inventive use for
prevention or treatment of disease, in particular for prevention or treatment of diabetes, and/or
reducing the absorption of glucose in the intestine, in particular in the small intestine, and/or
competitive suppression of sweet taste receptors in the intestine, in particular for competitive suppression of the T1R2/T1R3 receptors in the small intestine,
as described in each case above, does not however exclude the compounds excluded according to the above proviso or not designated above as preferred (unless otherwise indicated for individual compounds (see for example the compounds of formulas (X1) and (X2) above)).

Preference is for an inventive compound or mixture (as described above), wherein the compound or one, more or all compounds of the mixture is or are a lactisole precursor compound or lactisole precursor compounds, suitable (when administered orally) for releasing lactisole in the intestine. The advantages in this respect mentioned above of the compounds of formula (I) apply here by analogy.

Apart from this, for the inventive compounds of formula (I) or mixtures of these that are new compared with the prior art, that stated above for the inventive precursor compounds or mixtures for the prevention or treatment of disease or for reducing the absorption of glucose in the intestine or for competitive suppression of sweet taste receptors in the intestine also applies accordingly.

Particular preference is therefore for an inventive compound or mixture (as described above), wherein the radical R of the compound of formula (I) or one, more or all radicals R of the various compounds of formula (I) independently of one another contains or contain one or more —O— groups, which in each case independently of one another is or are a component or components of a hydroxy, ester or ether group.

Because of the advantageous effect of the compounds of formulas (1) to (6), in particular the compounds of formulas (1) to (4) (as described above), an inventive (as described above) compound or mixture is particularly preferred, wherein the precursor compound or one, more or all precursor compounds of the mixture is or are selected from the group comprising 2-(4-methoxyphenoxy)propanoic acid hexyl ester (compound of formula (1)), 2-(4-methoxyphenoxy)propanoic acid-2,3-bis-[2-(4-methoxyphenoxy)-propionyloxy]-propyl ester (compound of formula (2)), 2-(4-methoxyphenoxy)propanoic acid-2-[2-(4-methoxyphenoxy)-propionyloxy]-ethyl ester (compound of formula (3)), 2-(4-methoxyphenoxy)propanoic butyl ester (compound of formula (4)), 2-(4-methoxyphenoxy)propanoic acid-(E)-hex-2-enyl ester and 2-(4-methoxyphenoxy)-propanoic acid-2-isopropyl-5-methyl-phenyl ester, preferably from the group comprising the compounds of formulas (1) to (4)

(1)

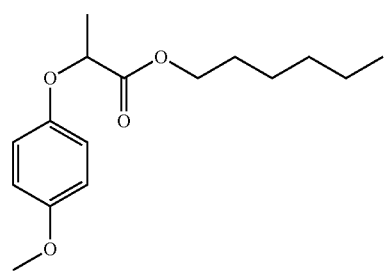

(2)

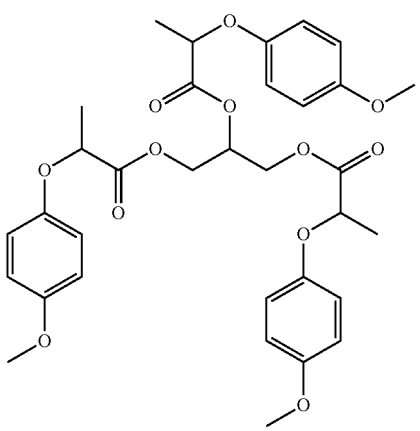

(3)

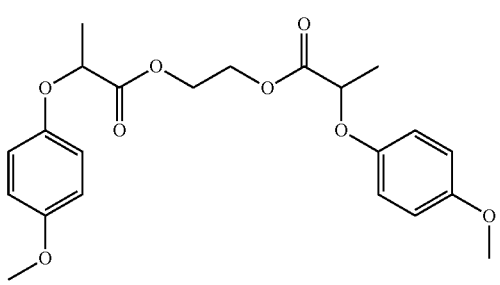

(4)

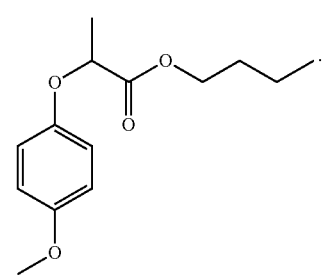

Quite particular preference is for the compound or a compound of the mixture to be a compound of formula (2).

As described above, particularly preferred compounds of formula (I) are also those which can be manufactured by esterification of partially or fully hydrolyzed edible fats or oils with lactisole.

Particular preference is also for an inventive compound or mixture (as described above), wherein the compound or one, more or all compounds of the mixture is or are selected from the group comprising compounds of formula

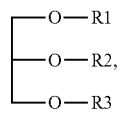

wherein one, more or all radicals R1 to R3 denote a lactisole group (2-(4-methoxyphenoxy)propionyloxy-) and the or possible other radicals R1, R2 and/or R3 in each case independently of one another denote either hydrogen or another organic radical, preferably a fatty acid radical. For preferred fatty acid radicals see above.

As described above, inventively preferred compounds of formula (I) are precursor compounds, preferably lactisole precursor compounds, which are suitable for releasing lactisole in the intestine. Apart from lactisole (as described above) in the (small) intestine one or more further components, in particular alcohols, is or are released. Preferred further components or alcohols released in the (small) intestine are mentioned above.

In accordance with the proviso that the radical R of an inventive compound of formula (I) does not denote methyl, ethyl or butyl (see above), it is preferably not a case of methanol, ethanol or butanol with the component(s) released in the (small) intestine.

Consequently, in connection with the present invention those compounds of formula (I) (as described above) are particularly preferred which are suitable for releasing in the intestine, apart from lactisole, one or more further components, wherein the further component(s) is (are) from the group comprising the following compounds (the four-digit FEMA number and the CAS number or E-number are given in brackets where these are available):

4-allyl-2,6-dimethoxyphenol [3655; 6627-88-9], 1-pentanol [2056; 71-41-0], 2-amyl-3-phenyl-2-propen-1-ol [2065; 101-85-9], 4-methoxybenzyl alcohol [2099; 105-13-5], benzyl alcohol [2137; 100-51-6], borneol [2157; 464-43-7, 507-70-0], campholene alcohol [3741; 1901-38-8], carvacrol [2245; 499-75-2], carveol [2247; 2102-59-2, 99-48-9], carvomenthol [3562; 499-69-4], chavicol [4075; 501-92-8], cinnamyl alcohol [2294; 104-54-1], citronellol [2309; 106-22-9], 1-alpha-citronellol [2980; 6812-78-8], o-cresol [3480; 95-48-7]. m-cresol [3530; 108-39-4], p-cresol [2337; 106-44-5], cymenol [3242; 1197-01-9]; decadienol [3911; 18409-21-7]; 1-decanol [2365; 112-30-1], 3-decanol [3605; 1565-81-7]; 1-decen-3-ol [3824; 51100-54-0]; (E)-2-decen-1-ol [4304; 22104-80-9]; (Z)-4-decen-1-ol [4349; 57074-37-0], dehydrodihydroionol [3446; 57069-86-0], dihydrocarveol [2379; 619-01-2], dihydroeugenol [3598: 2785-87-7], dihydrofarnesol [4031; 51411-24-6], dihydroionol [3627; 3293-47-8], syringol [3137; 91-10-1], dimethylbenzyl alcohol [3139; 536-50-5], 4-(1,1-dimethylethyl)phenol [3918; 98-54-4], 2,6-dimethyl-4-heptanol [3140; 108-82-7], 2,6-dimethyl-6-hepten-1-ol [3663; 36806-46-9], dimethylnonadienol [4102; 67845-50-5], 3,7-dimethyl-1-octanol [2391; 203-374-5], hotrienol [3830; 20053-88-7], 2-hydroxy-2-methyl-1-phenylpropane [2393; 100-86-7]; 2-hydroxypiperitone [4143; 490-03-9], 1-dodecanol [2617; 112-53-8], 2-(ethoxymethyl)phenol [3485; 20920-83-6], ethyl maltol [3487; 4940-11-8], 2-(3-ethoxy-4-hydroxyphenyl)-4-methyl-1,3-dioxolane [3838; 68527-76-4], 4-ethyl syringol [3671; 14059-92-8], ethyl guaiacol [2436; 2785-89-9]; 2-ethyl-1-hexanol [3151; 104-76-7], 3-ethyl-2-hydroxy-2-cyclopenten-1-one [3152; 21835-01-8]; 4-ethyl phenol [3156; 123-07-9], 3-ethyl thio butan-1-ol [4282; 117013-33-9], 2-ethyl fenchol [3491; 18368-91-7], eugenol [2467;

97-53-0], farnesol [2478; 4602-84-0], fenchol [2480; 1632-73-1], furfuryl alcohol [2491; 98-00-0], geraniol [2507; 106-24-1], glycerin [2525; 56-81-5], glyceryl monooleate [2526; 25496-72-4], guaiacol [2532; 90-05-1], (E,E)-hepta-2,4-dien-1-ol [4127; 33467-79-7], 2-heptanol [3288; 543-49-7], 3-heptanol [3547; 589-82-2], (Z)-4-hepten-1-ol [3841; 6191-71-5], 1-hepten-3-ol [4129; 4938-52-7], 1-heptanol [2548; 111-70-6], 1-hexadecanol [2554; 36653-82-4], (E,E)-hexa-2,4-dien-1-ol [3922; 111-28-4], 1-hexanol [2567; 111-27-3], 3-hexanol [3351; 623-37-0], 1-hexen-3-ol [3608; 4798-44-1], (E)-2-hexen-1-ol [2562; 2305-21-7], (Z)-2-hexenol [3924; 928-94-9], (Z)-3-hexen-1-ol [2563; 928-96-1], (E)-3-hexen-1-ol [4356; 928-97-2]; 5-hexen-1-ol [4351; 821-41-0], (E)-4-hexen-1-ol [3430; 928-92-7], (Z)-4-hexen-1-ol [3430; 928-91-6]; 4-hydroxybenzyl alcohol [3987; 623-05-2], hydroxycitronellol [2586; 107-74-4], alpha-ionol [3624; 25312-34-9], beta-ionol [3625; 22029-76-1]; isoamyl alcohol [2057; 123-51-3]; isoborneol [2158; 124-76-5]; isobutyl alcohol [2179; 78-83-1]; 4-methyl-1-phenyl-2-pentanol [2208; 7779-78-4]; isochavicol [4062; 539-12-8], isoeugenol [2468; 97-54-1], 2-propanol [2929; 67-63-0]; cuminol [2933; 536-60-7], o-cumenol [3461; 88-69-7], isopulegol [2962; 89-79-2], linalool oxide [3746; 1365-19-1, 5989-33-3], linalool [2635; 78-70-6], maltol [2656; 118-71-8], menthol [2665; 15356-60-2, 1490-04-6, 2216-51-5], 2-(l-menthoxy) ethanol [4154; 38618-23-4], menthyl lactate [3748; 59259-38-0], p-menthane-3,8-diol [4053; 42822-86-6], (−)-3-menthoxypropane-1,2-diol [3784; 87061-04-9], mercaptobutanol [3502; 37887-04-0], 3-mercaptohexanol [3850; 51755-83-0], 3-mercapto-2-methyl-1-butanol [3993; 227456-33-9]; 3-mercapto-3-methyl-1-butanol [3854; 34300-94-2]; 2-mercapto-2-methyl-1-pentanol [3995; 258823-39-1], 3-mercapto-2-methyl-1-pentanol [3996; 227456-27-1], 4-mercapto-4-methyl-2-pentanol [4158; 31539-84-1], creosol [2671; 93-51-6]; 4-vinyl guaiacol [2675; 7786-61-0], 2-methylbutan-1-ol [3998; 137-32-6], 3-methyl-2-butanol [3703; 598-75-4], 2-methylbut-2-en-1-ol [4178; 4675-87-0], prenol [3647; 556-82-1], 4-methyl-2,6-dimethoxyphenol [3704; 6638-05-7], 3-methyl-1-pentanol [3762; 589-35-5]; 2-phenyl-1-propanol [2732; 1123-85-9], 2-methyl-4-phenyl-2-butanol [3629; 103-05-9], 4-(methylthio)-butanol [3600; 20582-85-8], 2-(methylthio)ethanol [4004; 5271-38-5]; 3-methylthio-1-hexanol [3438; 51755-66-9], thioguaiacol [3210; 1073-29-6], 3-(methylthio)-propanol [3415; 505-10-2], myrtenol [3439; 515-00-4], neomenthol [2666; 2216-52-6], nerol [2770; 106-25-2], nerolidol [2772; 142-50-7, 7212-44-4, 40716-66-3], (3E,6Z)-nonadien-1-ol [3884; 53046-97-2]; (3Z,6Z)-nonad en-1-ol [3885; 76649-25-7], 2,6-nonadien-1-ol [2780; 7786-44-9], 2,4-nonadien-1-ol [3951; 62488-56-6], (2E,6Z)-nonadien-1-ol [2780; 28069-72-9], nonan-2-ol [3315; 628-99-9], nonan-1-ol [2789; 143-08-8], (Z)-2-nonen-1-ol [3720; 41453-56-9], (Z)-6-nonen-1-ol [3465; 35854-86-5], (E)-2-nonen-1-ol [3379: 31502-14-4], nopol [3938; 128-50-7], (E,E)-2,4-octadien-1-ol [3956; 18409-20-6], octan-1-ol [2800; 111-87-5], octan-2-ol [2801; 123-96-6], octan-3-ol [3581; 589-98-0], (E)-2-octen-1-ol [3887; 18409-17-1], (E)-2-octen-4-ol [3888; 4798-61-2], 1-octen-3-ol [2805; 3391-86-4], 3-octen-2-ol [3602; 76649-14-4], (Z)-3-octen-1-ol [3467; 20125-84-2], (Z)-5-octen-1-ol [3722; 64275-73-6], (Z)-4-octen-1-ol [4354; 54393-36-1], oleyl alcohol [4363; 143-28-2], 2-pentanol [3316; 6032-29-7], 1-penten-3-ol [3584; 616-25-1], cis-2-pentenol [4305; 1576-95-0], perilla alcohol [2664; 536-59-4], 2-phenethyl alcohol [2858; 60-12-8], phenol [3223; 108-95-2], 4-phenyl-2-butanol [2879; 2344-70-9], 4-phenyl-3-buten-2-ol [2880; 17488-65-2], 1-phenyl-3-methyl-2-pentanol [2883; 10415-87-9], 5-phenylpentanol [3618; 10521-91-2], 2-phenylphenol [3959; 90-43-7], 1-phenyl-1-propanol [2884; 93-54-9], 3-phenyl-1-propanol [2885; 122-97-4], phytol [4196; 150-86-7], pinocarveol [3587; 5947-36-4], p-menth-1-en-3-ol [3179; 491-04-3], 1-propanol [2928; 71-23-8], 4-propenyl-2, 6-dimethoxyphenol [3728; 20675-95-0], 2-ethoxy-5-(1-propenyl)phenol [2922; 94-86-0], propylene glycol mono- and diesters of fatty acids [4208], propylene glycol stearate [2942; 142-75-6], propylene glycol [2940; 57-55-6], 1-phenyl-2-pentanol [2953; 705-73-7], 2-propylphenol [3522; 644-35-9], 4-propylphenol [3649; 645-56-7], 4-propyl-2,6-dimethoxyphenol [3729; 6766-82-1], 3-hydroxyphenol [3589; 108-46-3], rhodinol [2980; 6812-78-8], 4-thujanol [3239; 546-79-2], santalol [3006; 11031-45-1, 115-71-9, 77-42-9], sorbitol [3029; 50-70-4; e420], sotolon [3634; 28664-35-9], styrallyl alcohol [2685; 98-85-1], 4-methyl-5-thiazoleethanol [3204; 137-00-8], p-menth-3-en-1-ol [3563; 586-82-3], 1-p-menthen-4-ol [2248; 562-74-3], p-menth-8-en-1-ol [3564; 138-87-4], p-menth-1-en-8-ol [3045, 98-55-5], tetrahydrofurfuryl alcohol [3056; 97-99-4], 3,7-dimethyloctan-3-ol [3060; 78-69-3], 1-isopropyl-4-methylbicyclo [3.1.0]hexan-3-ol [4079; 21653-20-3], thymol [3066; 89-83-8], 3,3,5-trimethylcyclohexan-1-ol [3962; 116-02-9], 3,5,5-trimethyl-1-hexanol [3324; 3452-97-9], 2,4,8-trimethylnona-3,7-dien-2-ol [4211; 479547-57-4], 2,4,8-trimethyl-7-nonen-2-ol [4212; 437770-28-0], 2,3,4-trimethyl-3-pentanol [3903; 3054-92-0], 2,3,6-trimethylphenol [3963; 2416-94-6], 2,4,6-trimethylphenol [4329; 527-60-6], 2-undecanol [3246; 1653-30-1], trans-undec-2-en-1-ol [4068; 37617-03-1], 1-undecanol [3097; 112-42-5], vanillin butylene glycol acetal [4023; 4359-31-3], vanillin menthoxypropane diol acetal [3904; 180964-47-0], vanillin propylene glycol acetal [3905; 68527-74-2], vanillyl alcohol [3737; 498-00-0], 2-pinen-4-ol [3594; 473-67-6], vetiverol [4217; 89-88-3], 4-vinylphenol [3739; 2628-17-3], 2,5-xylenol [3595; 95-87-4], 2,6-xylenol [3249; 576-26-1], 3,4-xylenol [3596; 95-65-8], 2',4',6'-trihydroxy-3-(p-hydroxyphenyl)propiophenone [4390; 60-82-2], (+/−)-ethyl-3-hydroxy-2-methyl butyrate [4391; 27372-03-8], 2,4-dimethyl-4-nonanol [4407; 74356-31-3], 8,9-p-menthen-1,2-diol [4409; 1946-00-5], decahydro-2,2,4,8-tetramethyl-4,8-methanoazulen-9-ol [4410; 56747-96-7], D-2,8-p-menthadien-1-ol [4411; 22771-44-4], (Z)-3-nonen-1-ol [4412; 10340-23-5], 3,4-dihydroxybenzoic acid [4430; 99-50-3], 3-hydroxybenzoic acid [4431; 99-06-9], 2-hydroxy-4-methoxybenzaldehyde [4435; 673-22-3], methyl 3-hydroxybutyrate [4450; 1487-49-6], ethyl 3-hydroxyoctanoate [4453; 7367-90-0], hydroxyacetone [4462; 116-09-6], 1-hydroxy-4-methyl-2-pentanone [4463; 68113-55-3], propylene glycol mono-2-methylbutyrate [4467; 923593-56-0 & 923593-57-1], propylene glycol monohexanoate [4469; 39556-41-7 & 170678-49-6], dodecyl lactate [4482; 6283-92-7], hexadecyl lactate [4483; 35274-05-6], hydroxycitronellal propylene glycol acetal [4485; 93804-64-9], citral glyceryl acetal [4486; 5694-82-6], propylene glycol monobutyrate [4488; 29592-95-8], 2-methoxy-6-(2-propenyl)phenol [4490; 579-60-2], (R)-(−)-1-octen-3-ol [4492; 3687-48-7], cubebol [4497; 23445-D2-5], (−)-sclareol [4502; 515-03-7], (+)-cedrol [4503; 77-53-2], (D)-limonen-10-ol [4504; 38142-45-9], p-menthan-7-ol [4507; 5502-75-0], p-menth-1-en-9-ol [4508; 18479-68-0], 2,2,6,7-tetramethylbicyclo[4.3.0]nona-4,9(1)-dien-8-ol [4521; 97866-86-9], 6-hydroxycarvone [4523; 51200-86-3], 2,6,6-trimethyl-2-hydroxycyclohexanone [4531; 7500-42-7], acetoin propylene glycol acetal [4532; 94089-23-3], (+/−)-n-lactoyl tyramine [4550; 781674-18-8], magnolol [4559; 528-43-8], ethyl 2-hydroxyethyl sulfide [4562; 110-77-0], 2-hydroxyethanethiol [4582; 60-24-2], linalool oxide pyranoid [4593; 14049-11-7], 2-hydroxy-5-methyl acetophenone [4594; 1450-72-2], ethyl 2-hydroxy-3-phenyl propionate [4598], (D)-trehalose [4600; 6138-23-4], (E)-3-nonen-1-ol [4605; 10339-61-4], ethyl-5-hydroxy octanoate [4610; 75587-05-2], (Z)-2-octen-1-ol [4615; 26001-58-1], (E)-2-tridecen-1-ol [4617; 68480-25-1], 2-(phenoxy)ethanol [4620; 122-99-6], (4-methylphenyl)methanol [4624; 589-18-4], thiophen-2-ylmethanol [4642; 636-72-6], 2-hydroxy-2-(4-hydroxy-3-methoxyphenyl)acetic acid [4660; 55-10-7], (4S)-4-hydroxy-4-[(E,3R)-3-hydroxybut-1-enyl]-3,5,5-trimethylcyclohex-2-en-1-one [4661; 23526-45-6], 1-(4-hydroxy-3-methoxyphenyl)decan-3-one [4665; 27113-22-0], (2R)-6-methyl-2-[(1R)-4-methyl-1-cyclohex-3-enyl]hept-5-en-2-ol [4666; 515-69-5], mannitol [E421]; isomalt [E953]; maltitol [E965]; lactitol [E966]; xylitol [E967]; erythritol [E968]; fructose [57-48-7]; glycose [50-99-7]; sucrose [57-50-1]; ethanediol [107-21-1].

A further aspect of the present invention concerns the use of an inventive precursor compound or a mixture of two or more precursor compounds (as described above), preferably an inventive compound of formula (I) or a mixture of two or more compounds of formula (I) (as described above), in particular one that is described as particularly preferred above, for the prevention or treatment of diabetes, in particular of Type 2 diabetes and/or to reduce the absorption of glucose in the intestine, in particular in the small intestine, and/or for competitive suppression of sweet taste receptors in the intestine, in particular for competitive suppression of the T1R2/T1R3 receptors in the small intestine.

A further aspect of the present invention concerns a method for (a) the treatment or prevention of disease, preferably the for the treatment or prevention of diabetes, in particular of Type 2 diabetes, (b) reducing the absorption of glucose in the intestine, in particular in the small intestine, and/or (c) competitive suppression of sweet taste receptors in the intestine, in particular for competitive suppression of the T1R2/T1R3 receptors in the small intestine, in humans or animals with the following step:
administration of an effective quantity
of a precursor compound
or
of a mixture of two or more precursor compounds,
as defined in each case above, preferably an inventive compound of formula (I) or a mixture of two or more compounds of formula (I) (as described above), in particular one of those described above as particularly preferred.

In addition, the present invention concerns a method (as described above) for (a) the treatment or prevention of disease, preferably for the treatment or prevention of diabetes, in particular of Type 2 diabetes.

(b) reducing the absorption of glucose in the intestine, in particular in the small intestine, and/or (c) competitive suppression of sweet taste receptors in the intestine, in particular for competitive suppression of the T1R2/T1R3 receptors in the small intestine, in humans or animals, requiring treatment with sweet taste receptor antagonists and/or diabetes treatment or prophylaxis.

Here, the precursor compounds are preferably administered in the form of an inventive preparation, in particular in the form of an inventive pharmaceutical preparation for oral application (as described above).

In addition, the present invention concerns
an inventive precursor compound
or
an inventive mixture of two or more precursor compounds,
as described in each case above, preferably as described as preferred above,
or
an inventive edible composition (as described above)
or
an inventive preparation for nutrition or pleasure or a pharmaceutical preparation (as described above)
for application in a method for (a) the treatment or prevention of disease, preferably for the treatment or prevention of diabetes, in particular of Type 2 diabetes, (b) reducing the absorption of glucose in the intestine, in particular in the small intestine, and/or (c) competitive suppression of sweet taste receptors in the intestine, in particular for competitive suppression of the T1R2/T1R3 receptors in the small intestine, in humans or animals requiring treatment with sweet taste receptor antagonists.

A further aspect of the present invention concerns the use of an inventive precursor compound or mixture (as described above), preferably an inventive compound of formula (I) or a mixture of two or more compounds of formula (I) (as described above), in particular one which is described above as particularly preferred, in a preparation for nutrition or pleasure or a pharmaceutical preparation.

In addition, the present invention concerns the use of an inventive precursor compound or mixture (as described above), preferably an inventive compound of formula (I) or a mixture of two or more compounds of formula (I) (as described above), in particular one which is described above as particularly preferred, for the manufacture of a pharmaceutical preparation (in particular a medicinal product) for the prevention or treatment of diabetes, in particular of Type 2 diabetes.

Particular preference is for an inventive use (as described above), wherein the pharmaceutical preparation (the medicinal product) is a preparation for oral application.

Also preferred is an inventive use (as described above), wherein the pharmaceutical preparation (the medicinal product) comes in a form that is selected from the group comprising: capsules, tablets, coated tablets, granulates, pellets, solid mixtures, dispersions in liquid phases, emulsions, powders, solutions and pastes.

In the following, inventive edible compositions, preparations for nutrition or pleasure or semi-finished products and inventive pharmaceutical preparations are described.

Consequently, the present invention also concerns an edible composition, a preparation for nutrition or pleasure or semi-finished product comprising (A)—a precursor compound
or
a mixture of two or more precursor compounds,
as described in each case above, preferably an inventive compound of formula (I) or a mixture of two or more compounds of formula (I) (as described above), in particular one which is described above as particularly preferred,
and
(B) one or more further edible components.

Preference according to the invention is for an edible composition (as described above), wherein the, or one, more or all the further edible components (B) is or are selected from the group comprising sweet tasting substances,
sweet smelling flavoring substances and
substances, preferably maltodextrins or starch, which release glucose when digested.

Particular preference is consequently for the use of the inventive (precursor) compounds, in particular the inventive compounds of formula (I), in combination with sweet tasting substances and/or flavoring substances, which are able to generate or impart a sweet smell, and/or (preferably) in combination with substances, preferably maltodextrins or starch, which release glucose (in particular in the oral cavity) when digested.

Here, the sweet tasting substances are preferably selected from the group comprising: sweet-tasting carbohydrates or sugars (saccharose, trehalose, lactose, maltose, melizitose, melibiose, raffinose, palatinose, lactulose, D-fructose, D-glucose, D-galactose, L-rhamnose, D-sorbose, D-mannose, D-tagatose, D-arabinose, L-arabinose, D-ribose, D-glyceraldehyde), sugar alcohols (e.g. erythritol, threitol, arabitol, ribitol, xylitol, sorbitol, mannitol, maltitol, dulcitol, lactitol), proteins (e.g. miraculin, pentadin, monellin, thaumatin, curculin, brazzein), sweeteners such as magap, sodium cyclamate, acesulfame K, neohesperidin dihydrochalcone, naringin dihydrochalcone, saccharin, saccharin sodium salt, aspartame, superaspartame, neotame, alitame, sucralose, lugduname, carrelame, sucrononate, sucrooctate, or naturally occurring sweeteners consisting of miraculin, curculin, monellin, mabinlin, thaumatin, curculin, brazzein, pentadin, D-phenylalanine, D-tryptophane, or extracts or fractions derived from natural sources containing these amino acids and/or proteins, neohesperidin dihydrochalcone, steviolgylcoside, stevioside, steviolbioside, rebaudioside, rebaudioside A, rebaudioside B, rebaudioside C, rebaudioside D, rebaudioside E, rebaudioside F, rebaudioside G, rebaudioside H, dulcoside, rubusoside, suavioside A, suavioside B, suavioside G, suavioside H, suavioside I, suavioside J, baiyunoside 1, baiyunoside 2, phlomisoside 1, phlomisoside 2, phlomisoside 3, phlomisoside 4, abrusoside A, abrusoside B, abrusoside C, abrusoside D, cyclocaryoside A and cyclocaryoside I, oslandin, polypodoside A, strogin 1, strogin 2, strogin 4, selligueanin A, dihydroquercetin-3-acetate, perillartine, telosmoside $A_{15}$, periandrin I-V, pterocaryoside, cyclocaryoside, mukurozioside, trans-anethol, trans-cinnamaldehyde, bryoside, bryonoside, bryonodulcoside, carnosifloside, scandenoside, gypenoside, trilobtain, phloridzin, dihydroflavanol, hematoxylin, cyanin, chlorogenic acid, albiziasaponin, telosmoside, gaudichaudioside, mogroside, hernandulcine, monatin, glycyrrhetin acid and derivatives and salts thereof and phyllodulcin, wherein in the case of the naturally occurring sweeteners extracts or enriched fractions of these extracts can be used, e.g. *Thaumatococcus* extracts (sweet prayers plant), extracts of *Stevia* ssp. (in particular *Stevia rebaudiana*), swingle extract (*Momordica* or *Siratia grosvenorii*, Luo-Han-Guo), extracts of *Glycerrhyzia* ssp. (in particular *Glycerrhyzia glabra*), *Rubus* ssp. (in particular *Rubus suavissimus*), citrus extracts, extracts of *Lippia dulcis* and Buddha tea extracts (*Hydrangea dulcis* or *Hydrangea macrophylla*).

Flavoring substances to be advantageously combined with the inventive precursor compounds, which are able to generate or impart a sweet taste impression, are preferably selected from the group comprising: vanillin, ethylvanillin, 2-hydroxy-4-methoxybenzaldehyde, ethylvanillin isobutyrate (=3-ethoxy-4-isobutyryloxybenzaldehyde), Furaneol® (2,5-dimethyl-4-hydroxy-3(2H)-furanone and derivatives, (e.g. homofuraneol, 2-ethyl-4-hydroxy-5-methyl-3(2H)-furanone), homofuronol(2-ethyl-5-methyl-4-hydroxy-3(2H)-furanone and 5-ethyl-2-methyl-4-hydroxy-3(2H)-furanone), maltol and derivatives (e.g. ethylmaltol), coumarin and derivatives, gamma-lactones (e.g. gamma-undecalactone, gamma-nonalactone), delta-lactones (e.g. 4-methyldeltalactone, massoilactone, deltadecalactone, tuberolactone), methyl sorbate, divanillin, 4hydroxy-2(or 5)-ethyl-5(or 2)-methyl-3(2H)-furanone, 2-hydroxy-3-methyl-2-cyclopentenone, 3-hydroxy-4,5-dimethyl-2(5H) furanone, fruit esters and fruit lactones (e.g. acetic acid n-butyl ester, acetic acid isoamyl ester, propionic acid ethyl ester, butyric acid ethyl ester, butyric acid n-butyl ester, butyric acid isoamyl ester, 3-methyl-butyric acid ethyl ester, n-hexanoic acid ethyl ester, n-hexanoic acid allyl ester, n-hexanoic acid n-butyl ester, n-octanoic acid ethyl ester, ethyl-3-methyl-3-phenyl glycidate, ethyl-2-trans-4-cis-decadienoate), 4-(p-hydroxyphenyl)-2-butanone, 1,1-dimethoxy-2,2,5-trimethyl-4-hexane, 2,6-dimethyl-5-hepten-1-al, and phenylacetaldehyde.

The inventive edible compositions, the preparations for nutrition or pleasure or semi-finished products are usually products that are intended to be introduced into the human oral cavity, to remain there for a certain time and then either be consumed (e.g. ready to eat foods, see below) or removed from the mouth (e.g. chewing gum). These products also include all goods or substances which are intended to be eaten, in a processed, part processed or unprocessed state by humans. Edible compositions are in particular products which are added to foodstuffs during their manufacture, preparation or processing and which are intended to be introduced into the human oral cavity, in particular with said foodstuff. Consequently such compositions can also contain in particular ready-to-serve or ready-to-consume preparations for nutrition or pleasure (ready-to-serve or ready-to-consume preparations for nutrition or pleasure are in the context of the present test in particular foods, especially ready-to-consume foods (see definition below)). In addition, such compositions can be a component of a semi-finished product, which if necessary can in turn be used for the manufacture of the ready-to-serve or ready to consume preparations for nutrition or pleasure (inventive ready-to-serve or ready-to-consume preparations for nutrition or pleasure and semi-finished products are described below).

Within the scope of the present text, "foods" are to be understood as being in particular substances which are intended to be swallowed and then digested by humans in the unchanged, prepared or processed state; in this respect, foods also include casings, coatings or other coverings which are intended to be swallowed as well or for which swallowing is to be anticipated. Particular products that are usually removed from the oral cavity again (e.g. chewing gums) are also to be understood as being foods within the scope of the present text, because it cannot be ruled out that they will not be swallowed at least partially.

A ready-to-consume food is to be understood as meaning a food that is already complete in respect of the substances that are significant for the taste. The term "ready-to-consume food" also includes drinks as well as solid or semi-solid ready-to-consume foods. Examples which may be mentioned are frozen products, which are defrosted prior to consumption and must be heated to consumption temperature. Products such as yoghurt or ice cream, but also chewing gums or hard caramels, belong to the ready-to-consume foods.

Within the scope of the present text a semi-finished product is taken to mean a product which because of a very high content of flavoring substances and flavorings is basically not suitable for use as a ready-to-consume food. Only by mixing with at least one further component (i.e. by reducing the concentration of the flavoring substances and/or flavorings concerned) and, if necessary, additional process stages (e.g. heating and freezing) is the semi-finished product converted into a ready-to-consume food. Examples of semi-finished products here are packet soups, extracts for baking and custard powders.

Chewing gums (as a preferred inventive food or preparation for nutrition or pleasure) generally comprise a chewing gum base, i.e. a chewing mass which becomes plastic when chewed, various types of sugar, sugar substitutes, other sweetly tasting substances, sugar alcohols (especially sorbitol, xylitol, mannitol), cooling active substances, taste modifiers for unpleasant taste impressions, other taste-modifying substances (for example inositol phosphate, nucleotides such as guanosine monophosphate, adenosine monophosphate or other substances such as monosodium glutamate or 2-phenoxypropionic acid), humectants, thickeners, emulsifiers, stabilizers, odor modifiers and flavorings (for example eucalyptus menthol, cherry, strawberry, grapefruit, vanilla, banana, citrus, peach, blackcurrant, tropical fruits, ginger, coffee, cinnamon, combinations (of the mentioned flavorings) with mint flavorings as well as spearmint and peppermint alone). The combination of flavorings with other substances, which have cooling, warming and/or mouthwatering properties, is also especially interesting.

Numerous different chewing gum bases are known from the prior art, in which a distinction has been made between so-called "chewing gum" and "bubble gum" bases, wherein the latter are softer so that these also allow bubbles to be blown. Common chewing gum bases currently comprise, besides traditionally used natural resins or natural latex chicle, mostly elastomers such as polyvinyl acetates (PVA), polyethylenes, (low or medium molecular) polyisobutenes polybutadienes, isobutene-isoprene copolymers (butyl rubber), polyvinylethylether (PVE), polyvinylbutylether, copolymers of vinyl esters and vinyl ethers, styrene-butadiene-copolymers (styrene-butadiene-rubber, SBR) or vinyl elastomers, for example those based on vinyl acetate/vinyl laurate, vinyl acetate/vinyl stearate or ethylene/vinyl acetate, and mixtures of so-called elastomers, for example, described in EP 0 242 325, U.S. Pat. No. 4,518,615, U.S. Pat. No. 5,093,136, U.S. Pat. No. 5,266,336 U.S. Pat. No. 5,601,858 or U.S. Pat. No. 6,986,709. In addition, chewing gum bases contain further ingredients for example (mineral) fillers, plasticizers, emulsifiers, antioxidants, waxes, fats or fatty oils, for example hardened (hydrogenated) vegetable or animal fats, mono-, di- or triglycerides. Suitable (mineral) fillers are for example calcium carbonate, titanium dioxide, silicon dioxide, talc, aluminum oxide, dicalcium phosphate, tricalcium phosphate, magnesium hydroxide and mixtures thereof. Suitable plasticizers or agents for preventing adhesion (detackifiers) are for example lanolin, stearic acid, sodium stearate, ethyl acetate, diacetine (gylcerol diacetate), triacetine (gylcerol triacetate), and triethyl citrate. Suitable waxes are for example paraffin wax, candelilla wax, carnauba wax, microcrystalline waxes and polyethylene waxes. Suitable emulsifiers are for example phosphatides such as lecithin, mono- and diglycerides of fatty acids, for example glycerol monostearate.

In the following suitable compositions for consumption preferred according to the invention are described. Here, basically, in selecting the precursor compound(s) or the compounds of formula (I) that stated above applies by analogy. The precursor compounds referred to above as preferred, in particular the compounds of formula (I), are consequently particularly preferably contained in component (A) of an inventive composition.

Inventive compositions (as described above) comprise as one or more further edible components preferably one or more solid carriers. Such compositions are also preferred spray-dried compositions.

In these preferred (preferably spray-dried) inventive compositions one or more or all of the carrier substances contained are selected from the group consisting of silicon dioxide (silicic acid, silica gel), carbohydrates and/or carbohydrate polymers (polysaccharides), cyclodextrins, starches, degraded starches (starch hydrolyzates, preferably maltodextrins and dextrins), chemically or physically modified starches, modified celluloses, gum arabic, Ghatti-gum, traganth, karaya, carrageenan, guar gum, locust bean gum, alginates, pectin, inulin and xanthan gum. Particularly preferred carrier substances are silicon dioxide, gum arabic and maltodextrins, wherein maltodextrins with DE (dextrose equivalent) values in the range of 5 to 20 are preferred. It is irrelevant, which plant is originally used for preparing the starch hydrolyzates from starch. Corn-based starches and starches of tapioca, rice, wheat or potatoes are suitable and readily available. The carrier substances can also act as a flow adjuvant, for example silicon dioxide.

The inventive edible compositions are preferably manufactured by spray-drying or by means of mechanical mixing processes, wherein simultaneously comminution of the existing particles (in particular of the abovementioned carriers) can take place). Inventive compositions comprising one or more edible solid carriers (as described above), manufactured by spray-drying are particularly preferred. Regarding spray drying, reference is made to U.S. Pat. No. 3,159,585, U.S. Pat. No. 3,971,852, U.S. Pat. No. 4,532,145 and U.S. Pat. No. 5,124,162.

Here, inventive spray-dried compositions having a mean particle size in the range of 30-300 μm and a residual moisture of less than or equal to 5 weight %, with reference to the total weight of the composition are particularly preferred.

Particular preference is for such a composition to have a weight ratio of the total quantity of component (A) to the total quantity of solid carriers in the composition, in each case in relation to the dry weight, in the range of 1:10 to 1:100,000, preferably in the range of 1:50 to 1:20,000, particularly preferably in the range of 1:100 to 1:5,000.

It is also preferred if the total quantity of component (A) and solid carriers in the inventive composition (as described above), in relation to the dry weight of the composition, is 70 to 100 weight %, preferably 85 to 100 weight %.

According to a further aspect of the present invention an inventive edible composition contains as one or more further edible components one or more volatile flavoring substances, e.g. an individual flavoring substance or a mixture of different volatile flavoring substances or a flavoring substance composition.

In the context of the present text inventive precursor compounds (as described above), in particular compounds of formula (I), should not be allocated to the further components (B).

Preferably one, more or all of the volatile flavoring substances contained in an inventive composition has or have a vapor pressure of greater than or equal to 0.01 Pa at 25° C., preferably a vapor pressure of greater than or equal to 0.025 Pa at 25° C. More preferably the volatile flavoring substance or substances has or have, but at least a majority of the volatile flavoring substances, a vapor pressure of greater than or equal to 1 Pa at 25° C.

Particularly preferred (volatile) flavoring substances can be found in, for example H. Surburg and J. Panten, Common Fragrance and Flavor Materials, 5$^{th}$ Ed., Wiley-VCH, Weinheim 2006. The following are listed by way of example: organic acids (saturated and unsaturated) such as butyric acid, acetic acid, methylbutyric acid, capronic acid; alcohols (saturated and unsaturated) such as ethanol, propylene glycol, octenol, cis-3-hexenol, benzyl alcohol; sulfides and disulfides such as dimethyl sulfide, difurfuryl disulfide, methylthiopropanal, thiols such as methylfuranthiol; pyrazines and pyrrolines such as methylpyrazine, acetylpyrazine, 2-propionylpyrroline, 2-acetylpyrroline.

According to the invention a flavoring composition can also be used as a component of an inventive composition in the form of reaction flavorings (Maillard products) and/or extracts and/or etheric oils from plants or plant parts or fractions thereof.

An inventive composition (as described above) comprising one or more volatile flavoring substance(s) or a flavor composition (and one or more edible carriers) is, according to a preferred, alternative embodiment of the present invention itself an (inventive) flavoring composition.

According to a further aspect of the present invention an inventive composition (as described above) is preferably a water-in-oil (W/O) emulsion. With regard to the preferred precursor compounds or mixtures contained that stated above applies by analogy.

According to the aspects of the present invention described above an edible composition (as described above) is particularly preferred wherein component (B) contains or comprises
one or more solid carriers and if necessary a flavoring composition (see above)
or
water, an oil phase, one or more W/O emulsifiers, if necessary one or more antioxidants and if necessary one or more substances for intensifying the antioxidant effect.

Here, the solid carrier substances and the aroma composition can contain or comprise one or more of the sweet tasting substances, sweet smelling flavoring substances and/or materials, preferably maltodextrin or starch, described above, which upon digestion releases glucose. In particular the solid carrier substances can be selected from substances which release glucose upon digestion.

Further, an inventive composition (as described above) is particularly preferred, wherein the component (B) contains or comprises one or more solid carrier substances and if necessary a flavor composition and the weight ratio of the total quantity of component (A) in the composition to the total quantity of solid carrier substances in the composition, in each case in relation to the dry weight of the composition, is in the range 1:10 to 1:100,000, preferably in the range 1:50 to 1:20000, particularly preferably in the range 1:100 to 1:5000.

Also preferred is an edible composition (as described above), wherein the total quantity of component (A) and solid carrier substances in the composition, in relation to the dry weight of the composition, is 70 to 100 weight %, preferably 85 to 100 weight %.

Further preferred is an edible composition (as described above), wherein
the total quantity of component (A) in relation to the total weight of the composition is 0.01 to 0.1 weight %
and
component (B)
in each case in relation to the total weight of the composition contains or (preferably) comprises
5 to 30 weight %, preferably 8 to 25 weight % water,
50 to 90 weight %, preferably 60 to 80 weight % oil phase,
0.1 to 5 weight % W/O emulsifier(s)
and
if necessary one or more antioxidants and if necessary one or more substances for intensifying the antioxidant effect.

The oil phase of such an inventive W/O emulsion preferably comprises a fatty oil and/or a flavoring composition. Oil phases comprising or consisting of a fatty oil and a flavoring composition are preferred, preferably a flavoring composition as described above.

Suitable fatty oils are, for example, edible oils, in particular vegetable oils. Suitable fatty oils are, for example, borage oil, thistle oil, peanut oil, hazelnut oil, coconut oil, pumpkin seed oil, linseed oil, corn oil, macadamia nut oil, almond oil, olive oil, palm kernel oil, pecan oil, pistachio oil, rapeseed oil, rice germ oil, sesame oil, soybean oil, sunflower oil, walnut oil or wheat germ oil, or fractions available from them. Liquid neutral esters based on medium chain fatty acids and glycerin, such as Miglyols (for example Miglyol 810, Miglyol 812), can also be used. Sunflower oil, palm kernel oil and rapeseed oil are preferred. Furthermore, fractionated coconut oils, which mainly contain fatty acid residues having 6 to 8 C-atoms, are preferably used. These distinguish themselves by their taste neutrality and their good oxidation stability.

The consumable W/O emulsifier is preferably selected from the group consisting of lecithin (E 322), mono- and diglycerides of edible fatty acids (E 471), acetic acid monoglycerides (E 472a), lactic acid monoglycerides (E 472b), citric acid monoglycerides (E 472c), tartaric acid monoglycerides (E 472d), diacetyl tartaric acid monoglycerides (E 472e), sorbitan monostearate (E 491).

Inventively preferred antioxidants and substances, which can enhance the antioxidative effect, are natural tocopherols and their derivates, tocotrienols, flavonoids, ascorbic acid and salts thereof, alpha-hydroxy acids (for example citric acid, lactic acid, malic acid, tartaric acid) and Na-, K- and Ca-salts thereof, ingredients isolated from plants, extracts or fractions thereof, for example, from tea, green tea, algae, grape seeds, wheat germs, rosemary, oregano, flavonoids, quercetin, phenolic benzyl amines. Furthermore, propyl gallate, octyl gallate, dodecyl gallate, butyl hydroxy anisole (BHA), butyl hydroxy toluene (BHT), lecithines, mono- and diglycerides of edible fatty acids esterified with citric acid, orthophosphates and Na-, K- and Ca-salts of monophosphoric acid and ascorbyl palmitate are suitable as antioxidants.

The inventive W/O emulsions are suitable in particular for applying to food surfaces, wherein the food has preferably a water content of up to 10 weight %, preferably up to 5 weight %. In a preferred embodiment, the inventive W/O emulsion has a sufficiently low viscosity at application temperature for this purpose, so that the application of the W/O emulsion by spraying is possible. Preferred foods, to whose surfaces an inventive W/O emulsion can be applied are, for example, crackers, chips (e.g. based on potatoes, corn, cereal or bread), extruded snack goods (e.g. flips) or leaching pastries (such as pretzel sticks). Inventive W/O emulsions, are normally applied to the food surfaces in an amount of 0.5 to 6 weight % based on the total weight of the food.

As already mentioned the present invention also concerns preparations for nutrition or pleasure, in particular ready-to-serve or ready-to-consume preparations and semi-finished products (as described above).

Particular preference is for a preparation for nutrition or pleasure or semi-finished product (as described above), comprising an edible inventive composition (as described above).

An inventive composition or preparation, in particular a preparation for nutrition or pleasure or a pharmaceutical preparation (as described above), preferably contains the inventive precursor compound or inventive precursor compounds to be used, in particular the compounds of formula (I), in an effective quantity. This means that in an inventive composition or particularly an inventive preparation the amount of precursor compounds contained is preferably high enough for the sweet taste receptor antagonists released in the intestine (following oral administration) (e.g. lactisole, see above) to significantly inhibit the sweet taste receptors in the intestine, in particular the T1R2/T1R3 receptors in the small intestine. It is further preferred if the sweet taste receptor antagonists released in the intestine are sufficient to reduce the absorption of glucose in the intestine, in particular in the small intestine.

Alternatively, an inventive preparation can also contain a total quantity of precursor compounds (as described above) which is below the effective quantity, so that only (when taken orally) in combination with other inventive preparations is the effective quantity threshold reached or exceeded.

Inventive preparations for nutrition or pleasure or semi-finished products are preferably sugar-containing, reduced sugar or sweetened sugar-free preparations or semi-finished products.

In the context of the present invention, the term "reduced sugar" means that the inventive preparation or semi-finished product preferably generally has markedly less sugar or calorific sweeteners than the normal preparation or semi-finished product.

Particular preference is for inventive preparations for nutrition or pleasure or semi-finished products (as described above), wherein component (B) contains or comprises
one or more sweet tasting substance(s)
and/or
one or more sweet smelling flavoring substances (flavoring substances which are able to generate or convey a sweet taste impression).

Preferred sweet tasting substances and sweet smelling flavoring substances which are able to generate or convey a sweet taste impression, are mentioned above.

In particular, special preference is for inventive (ready-to-serve or ready-to-consume) preparations for nutrition or pleasure (as described above), which in relation to the total weight of the preparation contain a total quantity of component (A) in the range 0.5 ppm to 5,000 ppm, preferably 5 ppm to 1,000 ppm, particularly preferably 50 ppm to 500 ppm.

In contrast inventive semi-finished products (as described above) in relation to the total weight of the semi-finished products preferably have a total quantity of component (A) in the range 5 ppm to 500,000 ppm, preferably 50 ppm to 100,000 ppm, and particularly preferably 250 ppm to 5,000 ppm.

Inventive semi-finished products, in particular those semi-finished products described above as preferred, are advantageously well suited to the production of (ready-to-serve or ready-to-consume) (preferably inventive) preparations for nutrition or pleasure.

The preparations for nutrition or pleasure within the meaning of the present invention are, for example, bakery products (for example bread, dry biscuits, cakes, other pastry products), confectionery (for example chocolates, chocolate bar products, other bar products, fruit gums, hard and soft caramels, chewing gum), alcoholic or non-alcoholic beverages (for example coffee, tea, wine, beverages containing wine, beer, beverages containing beer, liqueurs, spirits, brandies, fruit-containing beverages, isotonic beverages, soft drinks, nectars, fruit and vegetable juices, fruit or vegetable juice preparations), instant beverages (for example instant cocoa beverages, instant tea beverages, instant coffee beverages), meat products (for example ham, fresh or cured sausage preparations, spiced or marinated fresh or cured meat products), eggs or egg products (dried egg, egg white, egg yolk), cereal products (for example breakfast cereals, muesli bars, precooked ready rice products), dairy products (for example milk beverages, milk ice cream, yoghurt, kefir, curd cheese, soft cheese, hard cheese, dried milk powder, whey, butter, buttermilk, partially or fully hydrolyzed milk protein-containing products), products made from soya protein or other soya bean fractions (for example soya milk and products made therefrom, soya lecithin-containing preparations, fermented products such as tofu or tempe or products made therefrom, soy sauces), fruit preparations (for example jams, fruit ice cream, fruit sauces, fruit fillings), vegetable preparations (for example ketchup, sauces, dried vegetables, deep-frozen vegetables, precooked vegetables, preserved vegetables, cooked vegetables), snack articles (for example baked or fried potato chips or potato dough products, bread dough products, maize- or peanut-based extrudates), fat- or oil-based products or emulsions thereof (for example mayonnaise, remoulade, dressings, condiments), other ready-to-serve meals and soups (for example dried soups, instant soups, precooked soups), spices, seasoning mixtures and in particular powdered seasonings, which are for example used in snack food applications.

The inventive preparations for nutrition or pleasure for the purposes of the present invention may also be used in the form of capsules, tablets (uncoated and coated tablets, for example coatings resistant to gastric juices), sugar-coated tablets, granules, pellets, mixtures of solids, dispersions in liquid phases, as emulsions, as powders, as solutions, as pastes or as other swallowable or chewable preparations.

As mentioned above, the present invention also concerns pharmaceutical preparations, in particular pharmaceutical preparations for oral application. Such an inventive pharmaceutical preparation (for oral application) consists of
(A)—a precursor compound
or
a mixture of two or more precursor compounds,
as described above in each case, preferably an inventive compound of formula (I) or a mixture of two or more compounds of formula (I) (as described above), in particular one which is described above as particularly preferred,
and
(C) one or more pharmaceutically acceptable further components.

That stated for the pharmaceutical preparations described above applies here by analogy. Similarly that stated above for the precursor compounds or mixtures contained as component (A) applies by analogy.

An inventive pharmaceutical preparation can also preferably be in a form selected from the group comprising: capsules, tablets (uncoated and coated tablets, e.g. gastric juice-resistant coatings), sugar-coated pills, granules, pellets, solid mixtures, dispersions in liquid phases, emulsions, powders, solutions, pastes or other preparations that may be swallowed or chewed, used as prescription-only or over-the-counter medicinal products.

An inventive pharmaceutical preparation is also preferably a medicinal product for the treatment or prevention of diabetes, in particular for the treatment or prevention of Type 2 diabetes.

A further aspect of the present invention concerns a method for manufacturing (i) an inventive preparation for nutrition or pleasure or semi-finished product or (ii) an inventive pharmaceutical preparation (as described above in each case) comprising the following step:

mixing or applying
a precursor compound (as described above), preferably a compound of formula (I), or a mixture of two or more precursor compounds (as described above)
or
an edible inventive composition (as described above)
with one or more or to one or more
(i) further edible component(s)
or
(ii) pharmaceutically acceptable further component(s).

Preferably here, a quantity of precursor compound(s) or of inventive composition is used that is sufficient to manufacture a preparation or semi-finished product which contains an effective quantity (see above) of precursor compound(s).

The inventive compositions, preparations or semi-finished products (in each case as described above) will preferably be manufactured by initially dissolving or mixing the precursor compound(s) in ethanol and (if necessary demineralized and/or purified) water. Then the solutions are preferably converted into an (at least almost) solid composition or preparation preferably by a drying process, preferably a spray-drying, vacuum freezing, reverse osmosis, evaporation or other concentration process or a combination of said processes. Here the drying can take place with the help of carriers (e.g. starch, starch derivatives, maltodextrin, silica gel, see above) or auxiliaries (e.g. plant gums, stabilizers). The drying preferably takes place by means of spray drying or vacuum frozen drying.

Further normal active substances, raw materials or excipients for nutrition or pleasure or oral pharmaceutical preparations can be contained in quantities of between 0.9 and 99.999999 weight %, preferably 10 to 80 weight %, in relation to the total weight of the preparations. The preparations may also contain water in a quantity of up to 99.999999 weight %, preferably 5 to 80 weight %, in relation to the total weight of the preparation.

Further, inventive preparations (as described above) are particularly preferably manufactured by introducing the precursor compound(s), in particular the compounds of formula (I) or a mixture of these, as substance(s), as a solution or in the form of a mixture with a solid or liquid carrier in a base preparation for nutrition or pleasure or for pharmaceutical use (for oral application). Advantageously the inventive preparations in the form of solution can also be converted by spray drying into a solid preparation.

According to a further preferred embodiment of the present invention in order to manufacture the inventive preparations the precursor compounds and if necessary further components of the inventive preparation are firstly introduced into emulsions, into liposomes, e.g. based on phosphatidyl choline, into microspheres, into nanospheres or also into capsules, granules or extrudates from a matrix, e.g. from starch, starch derivates, cellulose and cellulose derivates such as hydroxypropyl cellulose, other polysaccharides such as alginate, natural fats, natural waxes such as beeswax or carnauba wax or from proteins like gelatine, suitable for nutrition and pleasure.

In a further preferred manufacturing method for inventive preparations the inventive precursor compounds are previously complexed with one or more suitable complexing agent(s), such as cyclodextrins or cyclodextrin derivates, preferably alpha- or betacyclodextrin, and used in this complex form.

As further components for inventive preparations for nutrition or pleasure, normal basic materials, auxiliary materials and additives for food or luxury food can be used, e.g., water, mixtures of fresh or processed, vegetable or animal basic materials or raw materials (such as raw, fried, dried, fermented, smoked and/or cooked meat, bone, cartilage, fish, vegetables, herbs, fruits, nuts, vegetable or fruit juices or vegetable pastes or their mixtures), digestible or indigestible carbohydrate (e.g. sucrose, maltose, fructose, glucose, dextrins, amylose, amylopectin, inulin, xylane, cellulose, tagatose), sugar alcohols (such as sorbitol, erythritol), natural or hardened fats (e.g. tallow, lard, palm oil, coconut oil, hardened vegetable fat), oils (such as sunflower oil, peanut oil, corn oil, olive oil, fish oil, soybean oil, sesame oil), fatty acids or their salts (e.g. potassium stearate), proteinogenic or non-proteinogenic amino acids and related compounds (e.g. gamma-aminobutyric acid, taurine), peptides (e.g., glutathione), native or processed proteins (such as gelatine), enzymes (e.g. peptidases), nucleic acids, nucleotides, other taste modifiers for unpleasant taste impressions, and other taste modulators for other, normally not unpleasant taste impressions, other taste-modulating substances (e.g. inositol phosphate, nucleotides such as guanosine monophosphate, adenosine monophosphate, or other substances such as monosodium glutamate or 2-phenoxypropionic acid), emulsifiers (for example, lecithins, diacylglycerols, gum arabic), stabilizers (e.g., carrageenan, alginate), preservatives (such as benzoic acid and its salts, sorbic acid), antioxidants (such as tocopherol, ascorbic acid), chelating agents (such as citric acid), organic or inorganic acidifiers (such as malic acid, acetic acid, citric acid, tartaric acid, phosphoric acid), additionally bitter substances (such as quinine, caffeine, limonin, amarogentin, humolone, lupolone, catechines, tannins), sweeteners (e.g. saccharin, cyclamate, aspartame, neotame), the enzymatic browning-prohibiting substances (e.g. sulfite, ascorbic acid), essential oils, plant extracts, natural or synthetic dyestuffs or pigments (such as carotenoids, flavonoids, anthocyans, chlorophyll and their derivates), spices, trigeminally effective substances or plant extracts containing such trigeminally effective substances, synthetic, natural or natural-identical flavorings or odorous substances and odor modifiers.

Chewing gums, as inventive preparations for nutrition or pleasure as described above) generally comprise a chewing gum base, i.e. a chewable mass which becomes plastic on chewing, sugars of various kinds, sugar substitutes, sweeteners, sugar alcohols, other taste-correcting agents for unpleasant taste impressions, taste-correcting agents for further, generally not unpleasant taste impressions, taste-modulating substances (for example inositol phosphate, nucleotides such as guanosine monophosphate, adenosine monophosphate or other substances, such as sodium glutamate or 2-phenoxypropionic acid), humectants, thickeners, emulsifiers, aromas, and stabilizers or odor-correcting agents.

According to a further aspect of the present invention the (inventive) precursor compounds, in particular the compounds of formula (I) (as described above), are preferably used in combination with one or more substances for altering, masking or reducing the unpleasant taste impression of an unpleasant tasting substances and/or to reinforce a pleasant taste impression of a pleasant tasting substance, wherein this or these further substance or substances is or are not inventive precursor compounds (as described above), in particular is or are not a compound or compounds of formula (I). Consequently advantageously any unpleasant notes of the (inventive) precursor compounds or in particular the compounds of formula (I) which may be present are reduced or (at least partly) masked. An inventive preparation or semi-finished product (as described above), which in component (B) or (C) contains one or more such substances, will be perceived by the consumer as more pleasant and of higher quality.

These substances or taste modifiers are preferably selected from the following list, without this limiting the present invention: nucleotides (e.g. adenosine 5'-monophosphate, cytidine 5'-monophosphate) or pharmaceutically acceptable salts thereof, sodium salts (e.g. sodium chloride, sodium lactate, sodium citrate, sodium acetate, sodium gluconate), hydroxy-flavanones, for example eriodictyol, sterubin (eriodictyol-7-methylether), homoeriodictyol, and the sodium, potassium, calcium or zinc salts thereof (in particular those described in EP 1258200, which as regards the corresponding compounds disclosed therein, is incorporated into the present application for reference), 2,4-dihydroxybenzoic acid vanillylamide, 2,4-dihydroxybenzoic acid N-(4-hydroxy-3-methoxybenzyl)amide, 2,4,6-trihydroxybenzoic acid N-(4-hydroxy-3-methoxybenzyl)amide, 2-hydroxybenzoic acid N-4-(hydroxy-3-methoxybenzyl)amide, 4-hydroxybenzoic acid N-(4-hydroxy-3-methoxybenzyl)amide, 2,4-dihydroxybenzoic acid N-(4-hydroxy-3-methoxybenzyl)amide monosodium salt, 2,4-dihydroxybenzoic acid N-2-(4-hydroxy-3-methoxyphenyl)ethylamide, 2,4-dihydroxybenzoic acid N-(4-hydroxy-3-ethoxybenzyl)amide, 2,4-dihydroxybenzoic acid N-(3,4-dihydroxybenzyl)amide and 2-hydroxy-5-methoxy-N-[2-(4-hydroxy-3-methoxyphenyl)ethylamide, 4-hydroxybenzoic acid vanillylamide (in particular those described in WO 2006/024587, which as regards the corresponding compounds disclosed therein, is incorporated into the present application for reference): hydroxydeoxybenzoins, such as 2-(4-hydroxy-3-methoxyphenyl)-1-(2,4,6-trihydroxyphenyl)ethanone, 1-(2,4-dihydroxyphenyl)-2-(4-hydroxy-3-methoxyphenyl)-ethanone, 1-(2-hydroxy-4-methoxyphenyl)-2-(4-hydroxy-3-methoxyphenyl)ethanone (in particular those described in WO 2006/106023, which as regards the corresponding compounds disclosed therein, is incorporated into the present application for reference); hydroxyphenyl alkane diones, such as gingerdion-[2], gingerdion-[3], gingerdion-[4], dehydrogingerdion-[2], dehydrogingerdion-[3], dehydrogingerdion-[4]) (in particular those as described in WO 2007/003527, which as regards the corresponding compounds disclosed therein, is incorporated into the present application for reference); diacetyl trimers (in particular those as described in WO 2006/058893 which as regards the corresponding compounds disclosed therein, is incorporated into the present application for reference); gamma-aminobutyric acids (in particular those as described in WO 2005/096841 which as regards the corresponding compounds disclosed therein, is incorporated into the present application for reference); divanillins (in particular those described in WO 2004/078302 which as regards the corresponding compounds disclosed therein, is incorporated into the present application for reference) and 4-hydroxydihydrochalcones, preferably as described in US 2008/227867 A1 (which as regards the corresponding compounds disclosed therein, is incorporated into the present application for reference, here in particular phloretin and davidigenin, amino acids or mixtures of whey proteins and lecithins, hesperitin as disclosed in WO 2007/014879, which as regards these compounds, is incorporated into the present application for reference, 4-hydroxydihydrochalcones as disclosed in WO 2007/107596, which as regards these compounds, is incorporated into the present application for reference, or propenylphenylglycosides (chavicolglycoside) as described in EP 1955601 A1, which as regards these compounds, is incorporated into the present application for reference, deoxybenzoins such as 2-(4-hydroxyphenyl)-1-(4-hydroxy-3-methoxyphenyl)ethanone (in particular as described in DE 102009002268.6 and the respective patent applications based thereon, which as regards the corresponding compounds disclosed therein is incorporated into the present application for reference), hydroxyflavanes such as 3',7-dihydroxy-4'-methoxyflavane (in particular as described in U.S. Provisional Application 61/178,667 and the patent applications based thereon, which as regards the corresponding compounds disclosed therein is incorporated into the present application for reference), umami compounds as described in WO 2008/046895 A1 and EP 1 989 944 A1, which in each case as regards these compounds is incorporated into the present application for reference, and umami compounds as described in U.S. Provisional Application 60/984,023 or U.S. Provisional Application 61/061,273 and the respective patent applications based thereon, which as regards the corresponding compounds disclosed therein is incorporated into the present application for reference.

BRIEF DESCRIPTION OF THE DRAWINGS

FIG. 1 shows the quantities of lactisole released from the compounds of formulas (1), (2), (3) and (4) in the course of the artificial digestion. In addition, the ratio of the measured quantities of lactisole to the theoretical maximum expected quantity released—the number of alcohol functions esterified with lactisole—was calculated.

FIG. 2 shows that the inventive compounds (and also lactisole) exerts no appreciable agonistic effect on the sweet taste receptor.

FIG. 3 shows that the inventive compounds of formulas (1) and (2)—unlike lactisole—do not themselves demonstrate any antagonistic effect (in the presence of the sweet tasting substance naringin dihydrochalcone used as an example). This confirms the usage possibilities of the inventive compounds of formula (I) for a desired selective antagonistic effect in the (small) intestine without inhibiting the sweet taste receptors in the oral cavity.

FIG. 4 shows that the compound 2 according to the invention, unlike lactisole, does not demonstrate any antagonistic effect in the presence of the sweet-tasting substance aspartame or sucrose used as an example and can thus function as a selective sweet taste receptor antagonist in the intestine. The dose-effect curve for aspartame or saccharose is not altered by the presence of 2.

In the following the invention is explained in more detail by way of examples. Unless otherwise stated, all information and data, in particular percentages and quantity details, refer to the weight.

EXAMPLES

General Process Specification for Manufacturing Compounds of Formula (I) as Described Above (AAV1)

Into a solution of 1.0 equivalent lactisole ((2-(4-methoxyphenoxy)propanoic acid) and 5 drops of N-methylformanilide in 2 ml/mmol dichloromethane 1.2 equivalents of oxalyl chloride are slowly dropped in. The reaction mixture is then stirred for 2 hours at room temperature and for a further 3 hours with recycling. Following removal of the excess solvent and if necessary oxalyl chloride and HCl a 1 M solution of the acid chloride in dichloromethane is manufactured.

Into a mixture of the alcohol intended for conversion with the acid chloride and triethyl amine (1.1 equivalents per available alcohol function) in 2 ml/mmol dichloromethane 1.2 equivalents (per available alcohol function) of the solution prepared above are slowly dropped into the acid chloride solution. Once the exothermic reaction has subsided, stirring takes place for a further five hours with recycling. Then the reaction mixture is diluted water and the organic phase is separated off.

The organic phase is then washed with saturated sodium hydrogen carbonate solution and dried over sodium sulfate. Following removal of the solvent and subsequent column chromatography purification (hexane/ethyl acetate) the desired (purified) lactisole esters are obtained.

Example 1

2-(4-methoxyphenoxy)propanoic acid butyl ester (Compound of Formula (4))

4.60 g (62.1 mmol) of 1-butanol as the alcohol intended for the conversion were converted according to General Process Specification 1. Following column chromatography purification 9.10 g (36.1 mmol) of compound (4) were obtained as a liquid.

$^1$H-NMR (400 MHz, CDCl$_3$): 0.89 (t, J=7.5 Hz, 3H); 1.31 (m, 2H); 1.59 (d, J=6.8 Hz, 3H); 1.59 (m, 2H); 3.75 (s, 3H); 4.14 (m, 2H); 4.67 (q, J=7.0 Hz, 1H); 6.78-6.85 (kB; 4H) ppm.

$^{13}$C-NMR (100 MHz, CDCl$_3$): 13.6 (CH$_3$); 18.7 (CH$_3$); 19.0 (CH$_2$); 30.6 (CH$_2$); 55.6 (CH$_3$); 65.0 (CH$_2$); 73.6 (CH); 114.6 (CH); 116.4 (CH); 151.8 (C); 154.4 (C); 172.5 (C=O) ppm.

Mass spectrum (EI): m/z (%)=252 (M$^+$, 84); 151 (86); 124 (87); 123 (100); 109 (42); 92 (20); 77 (26); 41 (22); 29 (24); 28 (61).

Example 2

2-(4-methoxyphenoxy)-propanoic acid hexyl ester (Compound of Formula (1))

6.40 g (62.6 mmol) of hexanol were converted according to General Process Specification 1. Following column chromatography purification 10.20 g (36.4 mmol) of the compound (1) were obtained as fluid.

$^1$H-NMR (400 MHz, CDCl$_3$): 0.77 (t, J=6.7 Hz, 3H); 1.24-1.29 (kB, 6H); 1.59 (d, J=6.7 Hz, 3H); 1.59 (m, 2H); 3.75 (s, 3H); 4.14 (m, 2H); 4.66 (q, J=6.9 Hz, 1H); 6.78-6.85 (kB; 4H) ppm.

$^{13}$C-NMR (100 MHz, CDCl$_3$): 14.0 (CH$_3$); 18.7 (CH$_3$); 22.5 (CH$_2$); 25.4 (CH$_2$); 28.5 (CH$_2$); 31.4 (CH$_2$); 55.6 (CH$_3$); 65.3 (CH$_2$); 73.6 (CH); 114.6 (CH); 116.4 (CH); 151.8 (C); 154.4 (C); 172.6 (C=O) ppm.

Mass spectrum (EI): m/z (%)=281 (18); 280 (M$^+$, 88); 151 (90); 124 (92); 123 (100); 109 (32); 77 (25); 43 (37); 41 (26); 28 (64).

Example 3

2-(4-methoxyphenoxy)propanoic acid-(E)-hex-2-enyl ester 3.30 g (32.9 mmol) of (E)-2-hexen-1-ol were converted according to General Process Specification 1. Following column chromatography purification 4.20 g (15.1 mmol) of the desired compound were obtained as a liquid.

$^1$H-NMR (400 MHz, CDCl$_3$): 0.88 (t, J=7.4 Hz, 3H); 1.38 (hex, J=7.4, 2H); 1.59 (d, J=6.8 Hz, 3H); 2.01 (m, 2H); 3.75 (s, 3H); 4.58 (m, 2H); 4.66 (q, J=6.8 Hz, 1H); 5.52 (m, 1H); 5.74 (m, 1H); 6.78-6.85 (kB; 4H) ppm.

$^{13}$C-NMR (100 MHz, CDCl$_3$): 13.6 (CH$_3$); 18.6 (CH$_3$); 22.0 (CH$_2$); 34.3 (CH$_2$); 55.6 (CH$_3$); 65.8 (CH$_2$); 73.6 (CH); 114.6 (CH); 116.4 (CH); 123.4 (CH); 137.0 (CH); 151.7 (C); 154.5 (C); 172.2 (C=O) ppm.

Mass spectrum (EI): m/z (%)=278 (M$^+$, 71); 151 (100); 124 (43); 123 (58); 119 (32); 109 (17); 77 (24); 55 (47); 41 (30); 28 (21).

Example 4

2-(4-methoxyphenoxy)-propanoic acid-2-isopropyl-5-methyl-phenyl ester 4.96 g (32.0 mmol) of thymol were converted according to General Process Specification 1. Following column chromatography purification 5.24 g (16.0 mmol) of the desired compound were obtained as a liquid.

$^1$H-NMR (400 MHz, CDCl$_3$): 1.07 (d, J=6.9 Hz, 3H); 1.11 (d, J=6.9, 3H); 1.77 (d, J=6.8 Hz, 3H); 2.27 (s, 3H); 2.77 (hept, J=6.9 Hz, 1H); 3.75 (s, 3H); 4.93 (q, J=6.8 Hz, 1H); 6.69-7.01 (kB, 7H) ppm.

$^{13}$C-NMR (100 MHz, CDCl$_3$): 18.7 (CH$_3$); 20.8 (CH$_3$); 22.9 (CH$_3$); 23.0 (CH$_3$); 26.7 (CH); 55.65 (CH$_3$); 73.7 (CH); 114.7 (CH); 116.4 (CH); 122.2 (CH); 126.4 (CH); 127.4 (CH); 136.6 (C); 137.0 (C); 147.4 (C); 151.7 (C); 154.7 (C); 171.3 (C=O) ppm.

Mass spectrum (EI): m/z (%)=328 (M$^+$, 32); 177 (24); 151 (48); 150 (24); 135 (13); 124 (100); 123 (14); 119 (23); 91 (14), 77 (22)

Example 5

2-(4-methoxyphenoxy)propanoic acid-2-[2-(4-methoxyphenoxy)-propionyloxy]-ethyl ester (Compound of Formula (3))

1.03 g (16.6 mmol) of glycol were converted according to General Process Specification 1. Following column chromatography purification 5.50 g (13.1 mmol) of compound (3) were obtained as a low viscosity liquid.

$^1$H-NMR (400 MHz, CDCl$_3$): 1.555 (d, J=6.8 Hz, 3H); 1.557 (d, J=6.8 Hz, 3H); 3.738 (s, 3H); 3.740 (s, 3H); 4.29-4.41 (kB, 4H); 4.63 (q, J=6.8 Hz, 1H); 4.64 (q, J=6.8 Hz, 1H); 6.77-6.85 (kB, 8H) ppm.

$^{13}$C-NMR (100 MHz, CDCl$_3$): 18.5 (CH$_3$); 55.6 (CH$_3$); 62.5 (CH$_2$); 73.4 (CH); 73.5 (CH); 114.7 (CH); 116.5 (CH); 116.6 (CH); 151.6 (C); 154.5 (C); 154.6 (C); 172.12 (C=O); 172.13 (C=O) ppm.

Mass spectrum (EI): m/z (%)=419 (29); 418 (M$^+$, 84); 223 (38); 177 (35); 151 (82) 124 (54); 123 (100); 99 (26); 77 (31); 28 (55).

Example 6

2-(4-methoxyphenoxy)propanoic acid-2,3-bis-[2-(4-methoxyphenoxy)-propionyloxy]-propyl ester (Compound of Formula (2))

1.04 g (11.1 mmol) of glycerin were converted according to General Process Specification 1. Following column chromatography purification 6.0 g (9.6 mmol) of compound (2) were obtained as a viscous liquid.

$^1$H-NMR (400 MHz, CDCl$_3$): 1.50-1.56 (kB, 9H); 3.72-3.75 (kB, 9H); 3.99-4.13 (kB, 2H); 4.26-4.32 (kB, 1H); 4.37-4.43 (kB, 1H); 4.54-4.69 (kB, 3H); 5.27 (m, 1H); 6.78-6.81 (kB, 12H) ppm.

$^{13}$C-NMR (100 MHz, CDCl$_3$): 18.44 (CH$_3$); 18.46 (CH$_3$); 18.50 (CH$_3$); 18.51 (CH$_3$); 18.54 (CH$_3$); 55.63 (CH$_3$); 55.65 (CH$_3$); 62.29 (CH$_2$); 62.34 (CH$_2$); 62.38 (CH$_2$); 69.55 (CH); 69.57 (CH); 73.12 (CH); 73.17 (CH); 73.23 (CH); 73.28 (CH); 73.33 (CH); 114.69 (CH); 114.74 (CH); 116.36 (CH); 116.39 (CH); 116.40 (CH); 116.42 (CH); 116.43f (CH); 116.47 (CH); 116.49 (CH); 151.48 (C); 151.49 (C); 154.56 (C); 154.58 (C); 154.60 (C); 154.61 (C); 171.42 (C=O); 171.44 (C=O); 171.45 (C=O); 171.48 (C=O); 171.72 (C=O); 171.75 (C=O); 171.77 (C=O); 171.79 (C=O); 171.81 (C=O) ppm.

Mass spectrum (LC-MS: C18; 100×2.1 mm; 0.2 ml/min; H$_2$O/CH$_3$CN 100/0→0/100, 15 min.): m/z (%)=646 (6); 645 (100); 433 (13); 432 (14); 431 (7) 430 (7).

Application Example 1

Influence of Compounds of Formula (I) (as Described Above) on the Sensorial Quality of Sweet Substances In order to quantify the influence of inventive compounds of formula (I) on the sensorial characteristics of various sweet tasting substances, in each case a sample (A) (sweet tasting substance) and a sample (B) (sweet tasting substance+compound of formula (I) or lactisole (as standard)) were sensorially assessed by a group of experts and rated according to their sweet taste impression on a scale of 1 [not sweet] to 10 [extremely sweet].

Then in each case from the average values of the assessments of samples (A) and (B) the change (in %) in the sweet taste impression was calculated.

1.0 g of the compound under investigation is vigorously stirred in 6.25 g artificial saliva [5.0 g potassium hydrogen carbonate; 0.64 g potassium chloride; 0.15 g sodium carbonate; 206.18 mg alpha-amylase (48.5 units); 100 mg mucin; distilled water to 1,000 ml] for 15 minutes at 37° C.

Then a (first) sample ("mouth", see below) is taken and the (remaining) mixture is adjusted with 10% hydrochloric acid to pH 2.5 and vigorously stirred with 20 ml of artificial gastric juice [0.88 g sodium chloride; 500 mg pepsin; distilled water to 100 ml; adjusted to pH 2.5 with 10% hydrochloric acid] for a further 4 hours at 37° C.

Then a (second) sample ("stomach", see below) is taken and the (remaining) mixture is adjusted with 10% sodium hydroxide solution to pH 7.5 and stirred intensely with 10 ml artificial intestinal juice [30 mg potassium chloride; 50 mg calcium chloride; 20 mg magnesium chloride; 100 mg sodium carbonate; 900 mg pancreatin; 900 mg bile, lyophilized; distilled water to 100 ml; pH 7.5, adjusted with 10% sodium hydroxide solution or 10% hydrochloric acid] for a further 3 hours at 37° C.

Then a (third) sample (intestine, see below) is taken.

The (three) samples taken are then in each case investigated using LC-MS, In order to quantify the lactisole (released) the UV spur was used.

FIG. 1 shows the quantities of lactisole released from the compounds of formulas (1), (2), (3) and (4) in the course of the artificial digestion. In addition the ratio of the measured quantities of lactisole to the theoretical maximum expected quantity released—the number of alcohol functions esterified with lactisole—was calculated.

From FIG. 1 it can be seen that from the compounds of formulas (1) to (4) under the (artificial) environmental conditions of the oral cavity ("mouth") no lactisole was released.

| Compound of formula (I) or lactisole/concentration | Sweet tasting substance/ concentration | Sweet taste impression (1-10) | | Change in sweet taste impression [%] |
|---|---|---|---|---|
| | | Sample A | Sample (B) | |
| Lactisole/10 mg/l | Sucrose/5% | 5.8 ± 1.2 | 4.2 ± 1.4 | −27% (p < 0.005) |
| Compound of formula (1), from example 2/14 mg/l | Sucrose/5% | 5.6 ± 1.4 | 5.0 ± 1 | −10% (insignificant) |
| Compound of formula (2), from example 6/10 mg/l | Sucrose/5% | 5.4 ± 1.5 | 5.6 ± 1.5 | 3% (insignificant) |
| Compound of formula (2), from example 6/10 mg/l | Naringin dihydrochalcone/ 50 mg/l | 5.1 ± 2.1 | 5.6 ± 2.1 | 9% (insignificant) |
| Compound of formula (4), from example 1/16 mg/l | Sucrose/5% | 5.8 ± 1.1 | 5.6 ± 1.5 | −5% (insignificant) |

Here it can be seen that the inventive compounds of formula (I) compared to the known sweet taste inhibitor lactisole have no significant influence on the sweet taste effect of the substances tested.

Application Example 2

Release of Lactisole from Compounds of Formula (I) During Artificial Digestion

An investigation was carried out on the release of lactose from the compounds of formulas (1), (2), (3) and (4) manufactured according to examples 1, 2, 5 and 6 in the process of artificial digestion. Lactisole was used as the (standard) reference and underwent artificial digestion in a similar manner.

In this connection, the term "artificial digestion" means the following method:

This result was confirmed in a further investigation by means of taste tests by a sensory panel: during the tasting of the compounds of formulas (1) to (4) no significant influence on the sweet taste intensity (in the oral cavity) was detected, while during the tasting of lactisole as expected a clear reduction in the sweet taste intensity was noticed. From this it can be concluded that during the tasting of the compounds of formulas (1) to (4) in the oral cavity no lactisole was released.

FIG. 1 also shows that neither did the compounds of formulas (1) to (4) under the (artificial) environmental conditions of the stomach passage ("stomach") release any lactisole.

Following addition of the artificial intestinal juice (and 3 hours of intense stirring at 37° C., see above), on the other hand, the release of lactisole from the compounds of formulas (1) to (4) could be observed (see FIG. 1, "Stomach"). In addition, from the data it can be inferred that the compound of formula (2) is particularly suited to the purposes of the present invention.

The results of the investigation confirm that the inventive application of compounds of formula (I) for (targeted) influencing of the sweet taste receptors in the intestine, without (when taken orally) impairing the sweet taste in the oral cavity.

Application Example 3

Investigation of the Inhibiting Effect of the Compounds of Formulas (1) to (4) on T1R2/T1R3 Receptors A stable cell line (HEK293TREX) extracted from human embryonic renal cells was manufactured with the help of the plasmid pIRESpuro3, coding for the G protein chimeras G15-Gi3. A further plasmid (pCDNA5-FRT), coding for the human TAS1R2 sequence, was also used. In this way it was possible to integrate the gene in a defined chromosomal region. The human TAS1R3 subunit of the human sweet taste receptor was cloned in pCDNA3-TO. This allowed the induction of the target gene using tetracycline. The stable, transfixed cell line was cultivated in high glucose content DMEM without tetracycline. For the measurements the cells were sown and cultivated (37° C., 5% $CO_2$) in polylysine-coated 96-well titrimetric places (black with transparent bases) until they achieved an 80% confluence. 24 h prior to the actual measurements the cells were incubated in low glucose content DMEM, GlutaMAX, 10% dialyzed FBS (Invitrogen, Carlsbad, Calif.) and tetracycline, in order to index the expression of the TAS1R3. A control sample of cells was not mixed with tetracycline (mock-cells). Approximately 2 hours prior to the measurement the cells were treated for 1 hour with the calcium-sensitive dye Fluo4-AM (2 µg/ml in DMEM, Molecular Probes, Carlsbad, Calif.). The cells were then washed three times with a solution C1 (130 mM NaCl, 5 mM KCl, 10 mM hepes, 2 mM $CaCl_2$, and 5 mM Glucose, pH 7.4). The calcium mobilization by receptor stimulation by the test substances was measured in an automated fluorometer (fluorometric imaging plate reader FLIPR, Molecular Devices, Sunnyvale, Calif.). The test substances were measured in a concentration of 1 mmol/l or 0.1 mmol/l in C1 solution. All data were determined in two independent experiments, which were each repeated three times. The calcium signals obtained were corrected for the proportion of the mock cells and (using the formula $\Delta F/F=(F-F_0)/F_0$) normalized on the starting intensity of the fluorescence prior to addition of the test substances ($F_0$).

FIG. 2 shows that the inventive compounds (and also lactisole) exert no appreciable agonistic effect on the sweet taste receptor.

FIG. 3 shows that the inventive compounds of formulas (1) and (2)—unlike lactisole—do not themselves demonstrate any antagonistic effect (in the presence of the sweet tasting substance naringin dihydrochalcone used as an example). This confirms the usage possibilities of the inventive compounds of formula (I) for a desired selective antagonistic effect in the (small) intestine without inhibiting the sweet taste receptors in the oral cavity.

Application Example 4

Spray-Dried Composition

| Component | Amount |
|---|---|
| Compound of formula (2) | 4 g |
| Maltodextrin | 96 g |

The two components are dissolved in a mixture of ethanol and demineralized water and then spray-dried.

Application Example 5

Aroma Composition

| Component | Amount |
|---|---|
| 10 weight % pellitorin in 1,2-propylene glycol/diethyl malonate | 0.25 g |
| Hesperetin | 2.50 g |
| Phloretin | 1.50 g |
| Compound of formula (2) | 1.50 g |
| Propylene glycol | 94.25 g |

The aroma composition was used in the application examples described in the following.

Application Example 6

Sugar-Free Chewing Gum

| Component | Ingredient | Weight % |
|---|---|---|
| A | Chewing gum base, "Jagum T" company | 30.00 |
| B | Sorbit, powdered | 39.00 |
|   | Isomalt ® (Palatinit GmbH) | 9.50 |
|   | Xylitol | 2.00 |
|   | Mannitol | 3.00 |
|   | Aspartame ® | 0.10 |
|   | Acesulfame ® K | 0.10 |
|   | Emulgum ® (Colloides Naturels, Inc.) | 0.30 |
| C | Sorbitol, 70% | 14.00 |
|   | Glycerin | 1.00 |
| D | Aroma composition, according to application example 5 | 1.00 |

Parts A to D are mixed and kneaded intensively. The raw material obtained can then for example be processed into thin strips of ready-to-consume chewing gum.

Application Example 7

Sugar-Free Hard Caramels

| Ingredient | Content [Weight %] |
|---|---|
| Palatinite, Type M | 75.07 |
| Water | 24.82 |
| Peppermint flavor | 0.1 |
| Compound of formula (2) | 0.01 |

First palatinate was mixed with water. The mixture was then melted at 165° C. followed by cooling to 115° C. The peppermint flavor and the compound of formula (2) were then added. Following blending the mixtures were poured into moulds, and after hardening removed from the moulds and then individually packed.

Application Example 8

Chocolate

A=dark chocolate
B=low-calorie dark chocolate
C=low-calorie dark chocolate
D=low-calorie dark chocolate
E=low-calorie full-milk chocolate

|   | Ingredient | A [weight %] | B [weight %] | C [weight %] | D [weight %] | E [weight %] |
|---|---|---|---|---|---|---|
|   | Cocoa butter | 13.50 | 13.00 | 13.50 | 9.48 | 14.00 |
| A | Cocoa paste | 42.00 | 39.00 | 42.00 | 44.00 | 23.00 |
|   | Erythritol | — | 47.45 | — | — | — |
|   | Maltitol, crystalline | — | — | — | 23.00 | — |
|   | Inulin | — | — | — | 23.00 | — |
|   | Sorbitol | — | — | 44.00 | — | — |
|   | Lactitole | — | — | — | — | 38.55 |
|   | Polydextrose | — | — | — | — | 9.70 |
|   | Full milk powder | — | — | — | — | 14.0 |
|   | Sucrose | 43.98 | — | — | — | — |
| B | Lecithin | 0.48 | 0.48 | 0.40 | 0.48 | 0.50 |
|   | Vanillin | 0.02 | 0.02 | 0.02 | 0.02 | 0.20 |
|   | Aspartame | — | 0.03 | 0.06 | — | 0.03 |
|   | Compound of formula (2) | 0.02 | 0.02 | 0.02 | 0.02 | 0.02 |

The ingredients of component A are mixed and kneaded with 3-25% of the total quantity of cocoa butter used (see above, 13.50 weight %) at 30 to 40° C. for 15 minutes. Then component A is worked with a preferably cooled roller, then conched for a further 18 to 25 hours at 50 to 80° C., wherein the remaining cocoa butter is added. Shortly before the end of the conching process (1 to 3 hours) the ingredients of component B are mixed in. Following cooling to between 28 and 31° C. the mass is poured into a mould and then fully cooled.

Application Example 9

Carbonated Drink (Flavor: Cola)

A=drink containing sugar
B=low-calorie drink
C=low-calorie drink
D=low-calorie drink
E=low-calorie drink

| Ingredient | A [weight %] | B [weight %] | C [weight %] | D [weight %] | E [weight %] |
|---|---|---|---|---|---|
| Phosphoric acid 85% | 0.635 | 0.635 | 0.635 | 0.635 | 0.635 |
| Citric acid, anhydrous | 0.064 | 0.064 | 0.064 | 0.064 | 0.064 |
| Caffeine | 0.064 | 0.064 | 0.064 | 0.064 | 0.064 |
| Sucrose | 63.600 | — | — | — | 12.9 |
| Sucralose | — | 0.126 | — | — | — |
| Erythritol | — | — | 6.000 | — | — |
| Aspartame | — | — | 0.350 | — | 0.07 |
| Stevioside | — | — | — | 0.300 | — |
| Acesulfame K | — | — | — | — | 0.07 |

-continued

| Ingredient | A [weight %] | B [weight %] | C [weight %] | D [weight %] | E [weight %] |
|---|---|---|---|---|---|
| Caramel | 0.800 | 0.800 | 0.800 | 0.800 | 0.800 |
| Drink emulsion, type: cola | 1.445 | 1.445 | 1.445 | 1.445 | 1.445 |
| Sodium benzoate | 0.106 | 0.106 | 0.106 | 0.106 | 0.106 |
| Compound of formula | 0.030 | 0.030 | 0.030 | 0.030 | 0.030 |
| Water | to 100 | to 100 | to 100 | to 100 | to 100 |

The solid components or ingredients are individually mixed with water, combined and made up to 100 g with water. The concentrate obtained is then allowed to age overnight at ambient temperature. Finally 1 part of concentrate is mixed with 5 parts of carbonated water, filled in bottles and sealed.

Application Example 10

Raspberry Jam (Suitable for Diabetics)

| Ingredients | [g] |
|---|---|
| Fructose, crystalline | 485.0 |
| Pectin | 6.5 |
| Sodium citrate | 1.0 |
| Water | 250.0 |
| Raspberries | 500.0 |
| Calcium lactate (3% solution) | 24 |
| Potassium sorbate (20% solution) | 5 |
| Compound of formula (2) | 0.1 |

30 g of fructose are initially dried with the pectin and the sodium citrate and then mixed again following addition of water. The raspberries are then added and the mixture heated to boiling point. The remaining 455.0 g of fructose and the calcium lactate are then added. The mixture is boiled down to a weight of 1,000 g, cooled slightly with vigorous stirring and mixed with calcium sorbate and the compound of formula (2). The mass is then filled in jars at a temperature of 80° C.

Application Example 11

Custard

A=full-sugar custard
B=low-sugar custard

| Ingredient | A [weight %] | B [weight %] |
|---|---|---|
| Sucrose | 7.8 | 5.4 |
| Starch | 3.0 | 3.0 |
| Skimmed milk powder | 1.5 | 1.5 |
| Aubygel MR50 | 0.5 | 0.5 |
| Extract of vanilla beans, spray-dried, Symrise | 0.1 | 0.1 |
| D-Tagatose | — | 0.1 |
| Symsweet HT 40% on maltodextrin | — | 0.04 |
| Compound of formula (2) | 0.005 | 0.005 |
| Milk, 1.5% fat | to 100 | to 100 |

The solid ingredients were produced and stirred into the milk. The mixture was heated to 95° C. for 2 minutes, stirring well, filled and cooled to between 5 and 8° C.

Application Example 12

Tabletop Sweetener

A=tabletop sweetener containing sugar
B=low-calorie tabletop sweetener
C=sugar-free tabletop sweetener

| Ingredient | A [weight %] | B [weight %] | C [weight %] |
|---|---|---|---|
| Sucrose | 98.75 | 48.75 | — |
| Fructose | — | 49.4 | — |
| Aspartame | — | 0.3 | — |
| Aspartame (spray-dried, 30% on maltodextrin) | — | — | 5.0 |
| Acesulfame | — | 0.3 | — |
| Maltodextrin | — | — | 93.75 |
| Spray-dried composition according to application example 4 | 1.25 | 1.25 | 1.25 |

All ingredients are mixed together and packaged in an airtight manner to offer protection from moisture.

Application Example 13

Vanilla Ice-Cream

A=Ice-cream (full sugar and full fat)
B, C, D, E=Low GI ice-cream

| Ingredients | A [weight %] | B [weight %] | C [weight %] | D [weight %] | E [weight %] |
|---|---|---|---|---|---|
| Maltitol | — | 10.0 | 10.0 | — | — |
| Sucrose | 16.0 | — | — | 10.0 | — |
| Fructose | — | — | — | — | 10.0 |
| Inulin | — | 6.7 | 6.7 | 6.7 | 6.7 |
| Skimmed milk powder | 12.0 | 3.68 | — | 3.68 | — |
| Milk protein, lactose <0.1% (Alaplex 1380 PPV; Frontera) | — | 3.68 | 7.36 | 3.68 | 7.36 |
| Cream (36% fat) | 25.0 | — | — | — | — |
| Coconut oil | — | 9.0 | 9.0 | 5.0 | 9.0 |
| Emulsifier (Grinsted HP 60, Danisco) | — | 0.285 | 0.285 | 0.285 | 0.285 |
| Emulsifier (Cremodan 709VEG, Danisco) | 0.5 | — | — | — | — |
| Guar gum | — | 0.0625 | 0.0625 | 0.0625 | 0.0625 |
| Carob bean gum | — | 0.145 | 0.145 | 0.145 | 0.145 |
| Carrageenan | 0.0175 | 0.0175 | 0.0175 | 0.0175 | 0.0175 |
| Vanillin | 0.011 | 0.011 | 0.011 | 0.011 | 0.011 |
| Aroma: vanilla | 0.16 | 0.16 | 0.16 | 0.16 | 0.16 |
| Beta-carotene 30% | 0.0042 | 0.0042 | 0.0042 | 0.0042 | 0.0042 |
| Compound of formula (2) | 0.01 | 0.01 | 0.01 | 0.01 | 0.01 |
| Water | to 100 | to 100 | to 100 | to 100 | to 100 |

For example A all ingredients are mixed at 60° C. For examples B to E firstly all ingredients as far as the oil and the emulsifier are mixed at 60° C. Then the emulsifier is mixed with the oil and afterwards mixed with the remaining quantity at 60° C. The mixture is now homogenized (150 bar/70° C.) and then pasteurized (83° C./20 s), before being cooled to 4° C. At this temperature the mixture is now aged for 5 hours before being frozen at −7° C. Then the mass is filled, shock frozen for 2 hours at −30° C. and stored at −25° C.

Application Example 14

Sweetener Tablets (64 mg)

| Ingredients | [weight %] |
|---|---|
| Sodium cyclamate | 66.59 |
| Saccharin, sodium salt | 7.35 |
| Neohesperidin dihydrochalcone | 0.11 |
| Lactose | 20.95 |
| Carboxymethyl cellulose, cross-linked | 3.5 |
| Spray-dried composition according to application example 4 | 1.5 |

The ingredients are mixed, pressed into tablet form and packaged.

Application Example 15

Currant Cookie

A=no-sugar
B=full-sugar

| | Ingredients | A [weight %] | B [weight %] |
|---|---|---|---|
| A | Margarine | 11.27 | 11.27 |
| | Skimmed milk powder | 1.71 | 1.71 |
| | Sucralose | 0.034 | — |

-continued

| | Ingredients | A [weight %] | B [weight %] |
|---|---|---|---|
| | Polydextrose | 24.21 | — |
| | Sucrose | — | 24.244 |
| | Salt | 0.550 | 0.550 |
| B | Whole egg | 9.370 | 9.370 |
| C | Flour | 28.32 | 28.32 |
| | Starch | 6.83 | 6.83 |
| | Sodium hydrogen carbonate | 0.376 | 0.376 |
| | Spray-dried composition according to application example 4 | 0.25 | 0.25 |
| D | Currants | 17.08 | 17.08 |

The ingredients are mixed together for 2 minutes. Following addition of the whole egg the mass is beaten for 3 minutes before the ingredients C are gradually mixed in. Finally the currents are added. The individual cookies are then divided up and baked at 220° C. for 10 minutes. Once they have cooled the cookies are packaged in airtight conditions.

Application Example 16

Tomato Ketchup

A=Tomato ketchup (full sugar)
B=Reduced sugar tomato ketchup
C=Reduced sugar tomato ketchup

| Ingredients | A [kg] | B [kg] | C [kg] |
|---|---|---|---|
| Tomato puree | 100.000 | 100.000 | 100.000 |
| Vinegar | 8.000 | 8.000 | 8.000 |
| Sugar | 15.000 | 11.500 | 5.000 |
| Glycyrrhizin | — | — | 0.014 |
| Hesperetin 2.5% in 1,2-propylene glycol | — | 0.235 | — |
| Phloretin 25% in 1,2-propylene glycol | — | 0.235 | — |
| Salt | 2.200 | 2.200 | 2.200 |
| Monosodium glutamate | 0.040 | 0.040 | 0.040 |
| Onion, puréed | 2.000 | 2.000 | 2.000 |
| Garlic, puréed | 0.100 | 0.100 | 0.100 |
| Cinnamon powder | 0.030 | 0.030 | 0.030 |

-continued

| Ingredients | A [kg] | B [kg] | C [kg] |
|---|---|---|---|
| Clove powder | 0.030 | 0.030 | 0.030 |
| Pepper (white), ground | 0.040 | 0.040 | 0.040 |
| Pepper (red), ground | 0.020 | 0.020 | 0.020 |
| Mace | 0.005 | 0.005 | 0.005 |
| Compound of formula (2) | 0.050 | 0.050 | 0.050 |

The ingredients are mixed in the order shown and the finished ketchup is homogenized with the help of an agitator, filled in bottles and sterilized.

Application Example 17

Chocolate Cake

A=chocolate cake (full sugar)
B=reduced sugar chocolate cake

| Ingredients | A [g] | B [g] |
|---|---|---|
| Sucrose | 180.0 | — |
| Lactitol monohydrate | — | 179.5 |
| Butter | 180.0 | 180.0 |
| Whole egg | 180.0 | 180.0 |
| Flour | 150.0 | 150.0 |
| Cocoa powder | 30.0 | 30.0 |
| Saccharin | 0.5 | 0.5 |
| Compound of formula (2) | 0.075 | 0.075 |

Sugar (or pre-mixed lactitol and saccharin) is beaten with the butter. Then the whole egg is added and likewise stirred in. Then the flour and the cocoa powder are gradually mixed in. The mass is then filled into a mould and baked for 60 minutes at 180° C.

Application Example 18

Investigations of the Activating or Inhibiting Effect of the Compounds of Formulas (1) to (4) on T1R2/T1R3 Receptors The same process as for application example 3 was used in order to demonstrate the effect of the substance according to its concentration on F/F.

FIG. 4 shows that the compound 2 according to the invention, unlike lactisole, does not demonstrate any antagonistic effect in the presence of the sweet-tasting substance aspartame or sucrose used as an example and can thus function as a selective sweet taste receptor antagonist in the intestine. The dose-effect curve for aspartame or saccharose is not altered by the presence of 2.

The invention claimed is:

1. A precursor compound of a sweet taste receptor antagonist, or a mixture of two or more precursor compounds of one or more different taste receptor antagonists, wherein the precursor compound is a lactisole-precursor compound which releases lactisole in the intestine, wherein the precursor compound or at least one precursor compound of the mixture is 2-(4-methoxyphenoxy)propanoic acid hexyl ester, 2-(4-methoxyphenoxy)propanoic acid-2,3-bis-[2-(4-methoxyphenoxy)-propionyloxy]-propyl ester, 2-(4-methoxyphenoxy)propanoic acid-2-[2-(4-methoxyphenoxy)-propionyloxy]-ethyl ester, 2-(4-methoxyphenoxy)propanoic acid-(E)-hex-2-enyl ester or 2-(4-methoxyphenoxy)-propanoic acid-2-isopropyl-5-methyl-phenyl ester.

2. A precursor compound of a sweet taste receptor antagonist, or a mixture of two or more precursor compounds of one or more different taste receptor antagonists, wherein the precursor compound is a lactisole-precursor compound which releases lactisole in the intestine, wherein the precursor compound or at least one precursor compound of the mixture is a compound of the formula

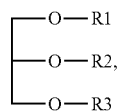

wherein at least one of the radicals R1 to R3 is a lactisole group (2-(4-methoxynhenoxy)propionyloxy-) and any remaining R1, R2 and/or R3 radicals are, independently of one another, either hydrogen or another organic radical.

3. The precursor compound, or a mixture of two or more precursor compounds according to claims 1 or 2 wherein the precursor compound or mixture of two or more precursor compounds release lactisole in the intestine for the prevention or treatment of diabetes.

4. The precursor compound or the mixture of two or more precursor compounds according to claim 1, wherein the precursor compound or a precursor compound of the mixture is a compound of formula (2)

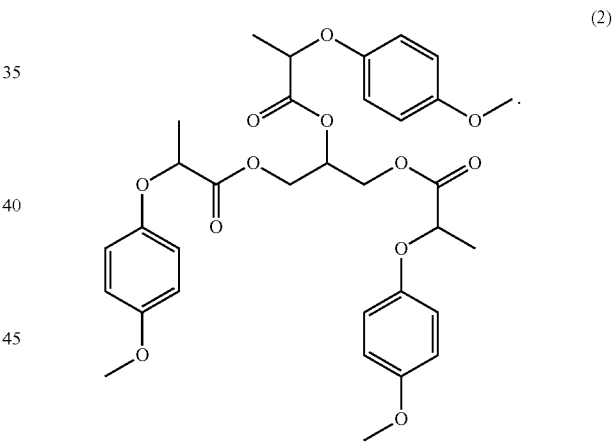

(2)

5. A composition which releases lactisole in the intestine following oral administration comprising the compound or mixture according to claims 1 or 2 wherein the compound or at least one compound of the mixture is a lactisole precursor compound and at least one further component, wherein the further component is 4-allyl-2,6-dimethoxyphenol, 1-pentanol, 2-amyl-3-phenyl-2-propen-1-ol, 4-methoxybenzyl alcohol, benzyl alcohol, borneol, campholene alcohol, carvacrol, carveol, carvomenthol, chavicol, cinnamyl alcohol, citronellol, 1-alpha-citronellol, o-cresol, m-cresol, p-cresol, cymenol, decadienol, 1-decanol, 3-decanol, 1-decen-3-ol, (E)-2-decen-1-ol, (Z)-4-decen-1-ol, dehydrodihydroionol, dihydrocarveol, dihydroeugenol, dihydrofarnesol, dihydroionol, syringol, dimethylbenzyl alcohol, 4-(1,1-dimethylethyl)phenol, 2,6-dimethyl-4-heptanol, 2,6-dimethyl-6-hepten-1-ol, dimethylnonadienol, 3,7-dimethyl-1-octanol, hotrienol, 2-hydroxy-2-methyl-1-phenylpropane, 2-hydroxypiperitone, 1-dodecanol, 2-(ethoxymethyl)phenol, ethyl maltol, 2-(3-ethoxy-4-hydroxyphenyl)-4-methyl-1,3-dioxolane, 4-ethyl syringol, ethyl guaiacol, 2-ethyl-1-hexanol, 3-ethyl-2-hydroxy-2-cyclopenten-1-one, 4-ethyl phenol, 3-ethyl thio butan-1-ol, 2-ethyl fenchol, eugenol, farnesol, fenchol, furfuryl alcohol, geraniol, glycerin, glyceryl monooleate, guaiacol, (E,E)-hepta-2,4-dien-1-ol, 2-heptanol, 3-heptanol, (Z)-4-hepten-1-ol, 1-hepten-3-ol, 1-heptanol, 1-hexadecanol, (E,E)-hexa-2,4-dien-1-ol, 1-hexanol, 3-hexanol, 1-hexen-3-ol, (E)-2-hexen-1-ol, (Z)-2-hexenol, (Z)-3-hexen-1-ol, (E)-3-hexen-1-ol, 5-hexen-1-ol, (E)-4-hexen-1-ol, (Z)-4-hexen-1-ol, 4-hydroxybenzyl alcohol, hydroxycitronellol, alpha-ionol, beta-ionol, isoamyl alcohol, isoborneol, isobutyl alcohol, 4-methyl-1-phenyl-2-pentanol, isochavicol, isoeugenol, 2-propanol, cuminol, o-cumenol, isopulegol, linalool oxide, linalool, maltol, menthol, 2-(1-menthoxy)ethanol, menthyl lactate, p-menthane-3,8-diol, (−)3 menthoxypropane-1,2-diol, mercaptobutanol, 3-mercaptohexanol, 3-mercapto-2-methyl-1-butanol, 3-mercapto-3-methyl-1-butanol, 2-mercapto-2-methyl-1-pentanol, 3-mercapto-2-methyl-1-pentanol, 4-mercapto-4-methyl-2-pentanol, creosol, 4-vinyl guaiacol, 2-methylbutan-1-ol, 3-methyl-2-butanol, 2-methylbut-2-en-1-ol, prenol, 4-methyl-2,6-dimethoxyphenol, 3-methyl-1-pentanol; 2-phenyl-1-propanol, 2-methyl-4-phenyl-2-butanol, 4-(methylthio)-butanol, 2-(methylthio)ethanol; 3-methylthio-1-hexanol, thioguaiacol, 3-(methylthio)-propanol, myrtenol, neomenthol, nerol, nerolidol, (3E,6Z)-nonadien-1-ol, (3Z,6Z)-nonadien-1-ol, 2,6-nonadien-1-ol, 2,4-nonadien-1-ol, (2E,6Z)-nonadien-1-ol, nonan-2-ol, nonan-1-ol, (Z)-2-nonen-1-ol, (Z)-6-nonen-1-ol, (E)-2-nonen-1-ol, nopol, (E,E)-2,4-octadien-1-ol, octan-1-ol, octan-2-ol, octan-3-ol, (E)-2-octen-1-ol, (E)-2-octen-4-ol, 1-octen-3-ol, 3-octen-2-ol, (Z)-3-octen-1-ol, (Z)-5-octen-1-ol, (Z)-4-octen-1-ol, oleyl alcohol, 2-pentanol, 1-pemen-3-ol, cis-2-pentenol, perilla alcohol, 2-phenethyl alcohol, phenol, 4-phenyl-2-butanol, 4-phenyl-3-buten-2-ol, 1-phenyl-3-methyl-3-pentanol, 5-phenylpentanol, 2-phenylphenol, 1-phenyl-1-propanol, 3-phenyl-1-propanol, phytol, pinocarveol, p-menth-1-en-3-ol, 1-propanol, 4-propenyl-2,6-dimethoxyphenol, 2-ethoxy-5-(1-propenyl)phenol, propylene glycol mono- and diesters of fatty acids, propylene glycol stearate, propylene glycol, 1-phenyl-2-pentanol, 2-propyl phenol, 4-propyl phenol, 4-propyl-2,6-dimethoxyphenol, 3-hydroxyphenol, rhodinol, 4-thujanol, santalol, sorbitol, sotolon, styrallyl alcohol, 4-methyl-5-thiazoleethanol, p-menth-3-en-1-ol, 1-p-menthen-4-ol, p-menth-8-en-1-ol, p-menth-1-en-8-ol, tetrahydrofurfuryl alcohol, 3,7-dimethyloctan-3-ol, 1-isopropyl-4-methylbicyclo[3.1.0]hexan-3-ol, thymol, 3,3,5-trimethylcyclohexan-1-ol, 3,5,5-trimethyl-1-hexanol, 2,4,8-trimethylnona-3,7-dien-2-ol, 2,4,8-trimethyl-7-nonen-2-ol, 2,3,4-trimethyl-3-pentanol, 2,3,6-trimethylphenol, 2,4,6-trimethylphenol, 2-undecanol, trans-undec-2-en-1-ol, 1-undecanol, vanillin butylene glycol acetal, vanillin menthoxypropane diol acetal, vanillin propylene glycol acetal, vanillyl alcohol, 2-pinen-4-ol, vetiverol, 4-vinylphenol, 2,5-xylenol, 2,6-xylenol, 3,4-xylenol, 2',4',6'-trihydroxy-3-(p-hydroxyphenyl)propiophenone, (+/−)-ethyl-3-hydroxy-2-methyl butyrate, 2,4-dimethyl-4-nonanol, 8,9-p-menthen-1,2-diol, decahydro-2,2,4,8-tetramethyl-4,8-methanoazulen-9-ol, d-2,8-p-menthadien-1-ol, (Z)-3-nonen-1-ol, 3,4-dihydroxybenzoic acid, 3-hydroxybenzoic acid, 2-hydroxy-4-methoxybenzaldehyde, methyl 3-hydroxybutyrate, ethyl 3-hydroxyoctanoate, hydroxyacetone, 1-hydroxy-4-methyl-2-pentanone, propylene glycol mono-2-methylbutyrate, propylene glycol monohexanoate, dodecyl lactate, hexadecyl lactate, hydroxycitronellal propylene glycol acetal, citral glyceryl acetal, propylene glycol monobutyrate, 2-methoxy-6-(2-propenyl)phenol, (R)-(−)-1-octen-3-ol, cubebol, (−)-sclareol, (+)-cedrol, (D)-limonen-10-ol, p-menthan-7-ol, p-menth-1-en-9-ol, 2,2,6,7-tetramethylbicyclo[4.3.0]nona-4,9(1)-dien-8-ol, 6-hydroxycarvone, 2,6,6-trimethyl-2-hydroxycyclohexanone, acetoin propylene glycol acetal, (+/−)-n-lactoyl tyramine, magnolol, ethyl 2-hydroxyethyl sulfide, 2-hydroxyethanethiol, linalool oxide pyranoid, 2-hydroxy-5-methylacetophenone, ethyl 2-hydroxy-3-phenylpropionate, (D)-trehalose, (E)-3-nonen-1-ol, ethyl 5-hydroxyoctanoate, (Z)-2-octen-1-ol, (E)-2-tridecen-1-ol, 2-(phenoxy)ethanol, (4-methylphenyl)methanol, thiophen-2-ylmethanol, 2-hydroxy-2-(4-hydroxy-3-methoxyphenyl)acetic acid, (4S)-4-hydroxy-4-[(E,3R)-3-hydroxybut-1-enyl]-3,5,5-trimethyl-cyclohex-2-e-n-1-one, 1-(4-hydroxy-3-methoxyphenyl)decan-3-one, (2R)-6-methyl-2-[(1R)-4-methyl-1-cyclohex-3-enyl]hept-5-en-2-ol, mannitol, isomalt, maltitol, lactitol, xylitol, erythritol, fructose, glycose, sucrose, or ethanediol.

6. A method of
(a) treating diabetes,
(b) reducing the absorption of glucose in the intestine, and/or
(c) competitively suppressing T1R2/T1R3 receptors in the small intestine of humans or animals by:
administering an effective quantity
of the precursor compound
or
of the mixture of two or more precursor compounds, according to claims 1 or 2.

7. A pharmaceutical preparation comprising the precursor compound or the mixture of two or more precursor compounds according to claims 1 or 2, wherein the pharmaceutical preparation is a preparation for an oral application.

8. A pharmaceutical preparation comprising the precursor compound or the mixture of two or more precursor compounds according to claims 1 or 2, wherein the pharmaceutical preparation is in the form of a capsule, a tablet, a coated tablet, a granulate, a pellet, a solid mixture, a dispersion in a liquid phases, an emulsion, a powder, a solution or a paste.

9. An edible composition, a preparation for nutrition or pleasure, or a semi-finished product comprising
(A)—the precursor compound
or
the mixture of two or more precursor compounds, according to claims 1 or 2 and
(B) at least one edible component.

10. The edible composition according to claim 9, wherein the edible component (B) is
a sweet tasting substance,
a sweet smelling flavoring substance or
a substance that releases glucose when digested.

11. The edible composition according to claim 9, wherein component (B) comprises
one or more solid carriers and optionally comprises a flavoring composition
or
water, an oil phase, one or more W/O emulsifiers, and optionally comprises one or more antioxidants and/or one or more substances for intensifying the antioxidant effect.

12. The edible composition according to claim 11, wherein the component (B) comprises one or more solid carrier substances and optionally comprises a flavoring composition wherein the weight ratio of the total quantity of component (A) in the composition and the total quantity of solid carrier substances in the composition, in relation to the dry weight of the composition, is in the range 1:10 to 1:100,000.

13. The edible composition according to claim 11, wherein the total quantity of component (A) and solid carrier substances in the composition, in relation to the dry weight of the composition, is 70 to 100 weight %.

14. The edible composition according to claim 11, wherein the composition optionally comprises one or more antioxidants and/or one or more substances for intensifying the antioxidant effect,
and
- the total quantity of component (A), in relation to the total weight of the composition, is 0.01 to 0.1 weight % and component (B) comprises
- 5 to 30 weight % water,
- 50 to 90 weight % oil phase,
- 0.1 to 5 weight % W/O emulsifier(s) in relation to the total weight of the composition.

15. The preparation for nutrition or pleasure according to claim 9, wherein the total quantity of component (A) in relation to the total weight of the preparation is in the range 0.5 ppm to 5,000 ppm.

16. The semi-finished product according to claim 9, wherein the total quantity of component (A) in relation to the total weight of the semi-finished product is in the range 5 ppm to 500,000 ppm.

17. A pharmaceutical preparation comprising,
(A)—the precursor compound
or
- the mixture of two or more precursor compounds, according to claims 1 or 2 and
- (C) one or more pharmaceutically acceptable components.

* * * * *